United States Patent
Stoll et al.

(10) Patent No.: US 11,588,076 B2
(45) Date of Patent: Feb. 21, 2023

(54) RADIATION-EMITTING OPTOELECTRONIC COMPONENT

(71) Applicant: OSRAM Opto Semiconductors GmbH, Regensburg (DE)

(72) Inventors: Ion Stoll, Tegernheim (DE); Alexander Baumgartner, Donaustauf (DE); Alexander Wilm, Regensburg (DE)

(73) Assignee: OSRAM OPTO SEMICONDUCTORS GMBH, Regensburg (DE)

( * ) Notice: Subject to any disclaimer, the term of this patent is extended or adjusted under 35 U.S.C. 154(b) by 580 days.

(21) Appl. No.: 16/606,226

(22) PCT Filed: Apr. 17, 2018

(86) PCT No.: PCT/EP2018/059773
§ 371 (c)(1),
(2) Date: Oct. 18, 2019

(87) PCT Pub. No.: WO2018/192922
PCT Pub. Date: Oct. 25, 2018

(65) Prior Publication Data
US 2021/0184082 A1    Jun. 17, 2021

(30) Foreign Application Priority Data
Apr. 18, 2017 (DE) .................. 10 2017 108 190.9

(51) Int. Cl.
*C09K 11/77* (2006.01)
*C09K 11/66* (2006.01)
(Continued)

(52) U.S. Cl.
CPC ............ *H01L 33/502* (2013.01); *C09K 11/08* (2013.01); *C09K 11/66* (2013.01);
(Continued)

(58) Field of Classification Search
CPC ....... H01L 33/28; H01L 33/32; H01L 33/502; H01L 33/504; C09K 11/08; C09K 11/66;
(Continued)

(56) References Cited

U.S. PATENT DOCUMENTS 10,505,080 B2 * 12/2019 Seibald ............ G02F 1/133609
10,711,192 B2 *  7/2020 Seibald ................ H01L 33/502
(Continued)

FOREIGN PATENT DOCUMENTS

| DE | 102014117423 A1 | 6/2016 |
| DE | 102015107593 A1 | 11/2016 |
| EP | 2753151 A1 | 7/2014 |

OTHER PUBLICATIONS

Wang et al., "Synthesis, structure and luminescence properties of SrSiAl2O3N2:Eu2+ phosphors for light-emitting devices and field emission displays", 2015, Dalton Transactions, Royal Society of Chemistry, 44, pp. 11057-11066. (Year: 2015).*

(Continued)

*Primary Examiner* — Matthew E. Hoban
*Assistant Examiner* — Lynne Edmondson
(74) *Attorney, Agent, or Firm* — Viering, Jentschura & Partner Mbb

(57) ABSTRACT

A radiation-emitting optoelectronic component may include a semiconductor chip or a semiconductor laser which, in operation of the component, emits a primary radiation in the UV region or in the blue region of the electromagnetic spectrum. The optoelectronic component may further include a conversion element comprising a first phosphor configured to convert the primary radiation at least partly to a first secondary radiation having a peak wavelength in the green region of the electromagnetic spectrum between 475 nm and 500 nm inclusive. The first phosphor may be or include $BaSi_4Al_3N_9$, $SrSiAl_2O_3N_2$, $BaSi_2N_2O_2$, $ALi_3XO_4$, (Continued)

$M^*_{(1-x^*-y^*-z^*)} Z^*_{z^*}[A^*_{a^*}B^*_{b^*}C^*_{c^*}D^*_{d^*}E^*_{e^*}N_{4-n^*}O_{n^*}]$, and combinations thereof.

14 Claims, 14 Drawing Sheets

(51) Int. Cl.
*C09K 11/08* (2006.01)
*H01L 33/50* (2010.01)
*C12M 1/00* (2006.01)
*H01L 33/28* (2010.01)
*H01L 33/32* (2010.01)
*H01S 5/323* (2006.01)

(52) U.S. Cl.
CPC .. *C09K 11/77342* (2021.01); *C09K 11/77346* (2021.01); *C09K 11/77347* (2021.01); *C09K 11/77348* (2021.01); *C12M 21/02* (2013.01); *C12M 31/10* (2013.01); *H01L 33/504* (2013.01); *H01L 33/28* (2013.01); *H01L 33/32* (2013.01); *H01S 5/32341* (2013.01)

(58) Field of Classification Search
CPC .............. C09K 11/665; C09K 11/7734; C09K 11/77348; C09K 11/7792; C12M 21/02; C12M 31/10; H01S 5/32341
See application file for complete search history.

(56) References Cited

U.S. PATENT DOCUMENTS

| | | | |
|---|---|---|---|
| 2010/0244067 A1* | 9/2010 | Winkler | C09K 11/7734 252/301.4 F |
| 2011/0278614 A1* | 11/2011 | Maier-Richter | H05B 33/10 524/440 |
| 2013/0277694 A1 | 10/2013 | Sakuta et al. | |
| 2015/0228869 A1* | 8/2015 | Yoo | H01L 25/0753 362/97.3 |
| 2016/0096991 A1 | 4/2016 | Hirosaki et al. | |

OTHER PUBLICATIONS

Paulusz, "Efficient Mn(IV) Emission in Fluorine Coordination", 1973, Journal of the Electrochemical Society, 120, pp. 942-947. (Year: 1973).*

International Search Report based on Application No. PCT/EP2018/059773, dated Dec. 19, 2018, 2 pages (English Transalation) (for reference purpose only).

German Search Report based on Application No. 10 2017 108 190.9, dated Mar. 21, 2018, 8 pages (for reference purpose only).

Singh, D. et al.; "LEDs for energy efficient greenhouse lighting", 2015; pp. 139-147; Renewable and Sustainable Energy Reviews, vol. 49, Elsevier Ltd.

Schulze, P.S.C. et al.; "Light emitting diodes (LEDs) applied to microalgal production"; dated Aug. 2014; pp. 422-430; CellPress, Trends in Biotechnology, vol. 32, Issue 8.

Ustin, S.L. et al.; "Retrieval of Foliar Information about Plant Pigment Systems from High Resolution Spectroscopy" dated Sep. 2009; 13 pages; Remote Sensing of Environment, vol. 113, Supplement 1, Elsevier Inc.

Zeinalov, Y. et al.; "On the action spectra of Photosynthesis and spectral dependence of the quantum efficiency", dated 2000; pp. 58-69; Bulg. J. Plant Physiol, 26(1-2), retrieved from https://pdfs.semanticscholar.org/7784/67ef2d52e7ef13ccb6ffdfb59ef21e79a5d8.pdf.

* cited by examiner

| rA | P |
|---|---|
| 0.1 | 99% |
| 0.2 | 98% |
| 0.25 | 97% |
| 0.3 | 94% |
| 0.5 | 66% |

| rA | P |
|---|---|
| 0.1 | 99% |
| 0.2 | 98% |
| 0.25 | 97% |
| 0.3 | 96% |
| 0.5 | 74% |

| rA | P |
|---|---|
| 0.1 | 99% |
| 0.2 | 97% |
| 0.25 | 95% |
| 0.3 | 88% |
| 0.5 | 59% |

| rA | P |
|---|---|
| 0.1 | 99% |
| 0.2 | 97% |
| 0.25 | 95% |
| 0.3 | 93% |
| 0.5 | 66% |

| rA | P |
|---|---|
| 0.1 | 99% |
| 0.2 | 97% |
| 0.25 | 95% |
| 0.3 | 93% |
| 0.5 | 68% |

| rA | P |
|---|---|
| 0.1 | 99% |
| 0.2 | 95% |
| 0.25 | 93% |
| 0.3 | 86% |
| 0.5 | 59% |

| rA | P |
|---|---|
| 0.1 | 99% |
| 0.2 | 97% |
| 0.25 | 95% |
| 0.3 | 89% |
| 0.5 | 66% |

| rA | P |
|---|---|
| 0.1 | 99% |
| 0.2 | 95% |
| 0.25 | 93% |
| 0.3 | 88% |
| 0.5 | 68% |

RADIATION-EMITTING OPTOELECTRONIC COMPONENT

CROSS-REFERENCE TO RELATED APPLICATIONS

The present application is a national stage entry according to 35 U.S.C. § 371 of PCT application No.: PCT/EP2018/059773 filed on Apr. 17, 2018; which claims priority to German Patent Application Serial No. 10 2017 108 190.9, which was filed on Apr. 18, 2017; both of which are incorporated herein by reference in their entirety and for all purposes.

TECHNICAL FIELD

The present invention relates to a radiation-emitting optoelectronic component and to a use of a radiation-emitting optoelectronic component for illumination of plants and microorganisms.

BACKGROUND

Energy-efficient light sources are of great importance for plant growth under artificial light sources. However, plants do not absorb all wavelengths of visible light with the same efficiency. Examples of important leaf dyes for photosynthesis include chlorophyll A, chlorophyll B, carotenoids, zeaxanthins, lycopenes and luteins. Overall, these dyes have their main absorptions in the range from 400 nm to 520 nm and 610 nm to 720 nm. However, there is a variation in the intensity of absorption in different plants and measurements. A number of characteristic absorptions can be found, for example, in Y. Zeinalov et al., Bulg. J. Plant Physiol., 2000, 26(1-2), 58-59; P. S. C. Schulze et al., Trends in Biotechnology, 2014, 32, 8, 422-430 and D. Singh et al., Renewable and Sustainable Energy Reviews, 49, 2015, 139-147. Typically, these leaf dyes can be efficiently stimulated to photosynthesize by lighting with blue and red LEDs. However, this has the disadvantage that the light is not white, which means that discolorations resulting, for example, from fungi or deficiency phenomena on the plant are not readily apparent to the user. In addition, this illumination leads to an ambient climate which is unpleasant to people.

SUMMARY

The object of at least one non-limiting embodiment is to provide a radiation-emitting optoelectronic component which is improved over the prior art.

The object is achieved by a radiation-emitting optoelectronic component having the features of claim 1 and the features of claim 12, and by the use of a radiation-emitting optoelectronic component having the features of claim 13.

A radiation-emitting optoelectronic component is specified. The radiation-emitting optoelectronic component includes a semiconductor chip or a semiconductor laser which, in operation of the component, emits a primary radiation in the UV region or in the blue region of the electromagnetic spectrum.

Here and hereinafter, the UV region of the electromagnetic spectrum refers to the wavelength range between 350 nm and 424 nm inclusive, and the blue region of the electromagnetic spectrum to the wavelength range between 425 and 475 nm inclusive. In a non-limiting embodiment, the peak wavelength of the primary radiation is in the range from 350 nm to 424 nm inclusive or in the range from 425 to 475 nm inclusive. The full width at half maximum (FWHM) for a semiconductor chip may range from 15 to 45 nm. In the case of a semiconductor laser, the full width at half maximum may be below 15 nm, for example between 1 nm and 15 nm.

In one embodiment, the component includes a conversion element including a first phosphor. The first phosphor is configured to convert the primary radiation at least partly to a first secondary radiation having a peak wavelength in the green region of the electromagnetic spectrum between 475 nm and 500 nm inclusive.

The fact that a phosphor at least partly converts the primary radiation to a secondary radiation may mean firstly that the primary radiation is partly absorbed by the phosphor and emitted as secondary radiation in a wavelength range at least partly different than the primary radiation, especially a longer wavelength range. In this embodiment, the component may emit a total radiation composed of the primary and secondary radiation.

The fact that a phosphorate at least partly converts the primary radiation to a secondary radiation may also mean that the primary radiation is absorbed virtually completely by the phosphor and released in the form of a secondary radiation. The total radiation emitted by the radiation-emitting optoelectronic component in this embodiment thus corresponds completely or virtually completely to the secondary radiation. Virtually complete conversion is understood to mean a conversion of more than 90%, especially more than 95%.

"Peak wavelength" in the present context refers to the wavelength of a peak of an emission of a semiconductor chip or a semiconductor laser or a phosphor at which the maximum intensity of emission lies. The peak wavelength is thus an absolute maximum in the emission spectrum, based in each case on the emission of the semiconductor chip or the semiconductor laser or the phosphor. The peak wavelength thus gives the wavelength of the main peak of an emission of the semiconductor chip or the semiconductor laser or the phosphorate which the maximum intensity of emission lies.

The remarks which follow describe compositions of a first phosphor and of a second phosphor and further phosphors in terms of empirical formulae. These each corresponds to the nominal composition of the materials. In fact, the exact atomic ratios may differ slightly from the ideal values stated. A possible value for such a deviation is, for example, 10%. It is likewise possible that the phosphors contain other further elements that are introduced, for example, via impurities or fluxes in the starting mixture or during the synthesis, especially (but not exclusively) boron and/or carbon and/or nitrogen and/or halogens, for example fluorine or chlorine or bromine. Any evaporation of individual components during the synthesis may also result in statistical underpopulation of individual layers. For reasons of clarity, these possible effects are not mentioned, by way of simplification, explicitly every time in the empirical formulae stated hereinafter.

In at least one embodiment, the first phosphor is selected from a group including $BaSi_4Al_3N_9$, an Sr—SiAlON (e.g. $SrSiAl_2O_3N_2$), $BaSi_2N_2O_2$, $ALi_3XO_4$, $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ and combinations thereof, where A is at least one element selected from the group consisting of Li, Na, K, Rb, Cs and combinations thereof, where X is at least one element selected from the group consisting of Si, Ge, Ti, Zr, Hf and combinations thereof;

where M* is selected from the group including Ca, Sr, Ba and combinations thereof, where Z* is selected from the group including Na, K, Rb, Cs, Ag and combinations thereof, where A* is selected from the group including Mg, Mn, Zn and combinations thereof, where B* is selected from the group including B, Al, Ga and combinations thereof, where C* is selected from the group including Si, Ge, Ti, Zr, Hf and combinations thereof, where D* is selected from the group including Li, Cu and combinations thereof, where E* is selected from the group including P, V, Nb, Ta and combinations thereof, and where:

$0 \le x^* \le 0.2$;

$0 \le y^* \le 0.2$;

$0 \le x^* + y^* \le 0.4$;

$0 \le z^* < 1$, $0 \le n^* \le 4$;

$0 \le a^* \le 4$;

$0 \le b^* \le 4$;

$0 \le c^* \le 4$;

$0 \le d^* \le 4$;

$0 \le e^* \le 4$;

$a^* + b^* + c^* + d^* + e^* = 4$;

$2a^* + 3b^* + 4c^* + d^* + 5e^* = 10y^* - n^* + z^*$;

where $BaSi_4Al_3N_9$, $SrSiAl_2O_3N_2$, $BaSi_2N_2O_2$, $ALi_3XO_4$ and $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ may each independently be doped with a rare earth element.

In a non-limiting embodiment, $BaSi_4Al_3N_9$, $SrSiAl_2O_3N_2$, $BaSi_2N_2O_2$, $ALi_3XO_4$ and $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ are independently doped with $Eu^{2+}$.

More particularly, A is selected from a group including Na, K and/or Li or combinations thereof. For example, A=Na, K and/or Li.

An Sr—SiAlON is a phosphor that includes Sr, Si, Al, O and N and may additionally be doped with a rare earth element, for example with $Eu^{2+}$. In the present context, an Sr—SiAlON may include $SrSiAl_2O_3N_2$.

These first phosphors can convert the primary radiation at least partly to a first secondary radiation having a peak wavelength in the green region of the electromagnetic spectrum between 475 nm and 500 nm inclusive. The peak wavelength position can especially be adjusted via the molar amount of $Eu^{2+}$, which is preferably within a range from 0.1 to 10 mol % with respect to Ba in $BaSi_4Al_3N_9:Eu^{2+}$, Sr in $SrSiAl_2O_3N_2:Eu^{2+}$, Ba in $BaSi_2N_2O_2:Eu^{2+}$ and A in $ALi_3XO_4:Eu^{2+}$.

In at least one embodiment, the first phosphor is selected from a group including $BaSi_4Al_3N_9:Eu^{2+}$, $SrSiAl_2O_3N_2:Eu^{2+}$, $BaSi_2N_2O_2:Eu^{2+}$, $ALi_3XO_4:Eu^{2+}$ and combinations thereof where A is at least one element selected from the group consisting of Li, Na, K, Rb, Cs and combinations thereof, where X is at least one element selected from the group consisting of Si, Ge, Ti, Zr, Hf and combinations thereof.

$ALi_3XO_4$ may be or include $A_2Li_6Si_2O_8$ (=$ALi_3XO_4$ with X=Si) where A is at least one element selected from the group including Li, Na, K, Rb, Cs and combinations thereof.

In at least one embodiment, $ALi_3XO_4$ is selected from a group including $NaLi_3SiO_4:Eu^{2+}$, $NaK(Li_3SiO_4)_2:Eu^{2+}$, $RbNa_3(Li_3SiO_4)_4:Eu^{2+}$, $CsKNa_2(Li_3SiO_4)_4:Eu^{2+}$, $RbKNa_2(Li_3SiO_4)_4:Eu^{2+}$, and $CsRbNaLi(Li_3SiO_4)_4:Eu^{2+}$.

In at least one embodiment, portions of the oxygen in $ALi_3XO_4$ are replaced by nitrogen. The excess negative charge can be balanced, for example, by a metal that is not an alkali metal (for example by an alkaline earth metal or a transition metal). In this case, the phosphor is an oxynitridic phosphor. For example, up to 50 atom %, e.g. up to 25 atom %, of the oxygen may be replaced by nitrogen. $ALi_3XO_4$ may alternatively be free of nitrogen.

In at least one embodiment, the first phosphor is a phosphor of the following general formula:

$$M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$$

where M* is selected from the group including Ca, Sr, Ba and combinations thereof, where Z* is selected from the group including Na, K, Rb, Cs, Ag and combinations thereof, where A* is selected from the group including Mg, Mn, Zn and combinations thereof, where B* is selected from the group including B, Al, Ga and combinations thereof, where C* is selected from the group including Si, Ge, Ti, Zr, Hf and combinations thereof, where D* is selected from the group including Li, Cu and combinations thereof, where E* is selected from the group including P, V, Nb, Ta and combinations thereof, and where:

$0 \le x^* \le 0.2$;

$0 \le y^* \le 0.2$;

$0 \le x^* + y^* \le 0.4$;

$0 \le z^* < 1$, $0 \le n^* \le 4$;

$0 \le a^* \le 4$;

$0 \le b^* \le 4$;

$0 \le c^* \le 4$;

$0 \le d^* \le 4$;

$0 \le e^* \le 4$;

$a^* + b^* + c^* + d^* + e^* = 4$;

$2a^* + 3b^* + 4c^* + d^* + 5e^* = 10y^* - n^* + z^*$, wherein the phosphor may be doped with a rare earth element, for example a rare earth element selected from the group including: Ce, Eu, Yb and combinations thereof.

In a non-limiting embodiment, $z^* \le 0.9$; for example, $z^* \le 0.5$. In another non-limiting embodiment, $x^* + y^* + z^* \le 0.2$.

In yet another non-limiting embodiment, $2 \le a^* \le 3$.

In at least one embodiment, the phosphor has a crystal structure similar to the crystal structure of the $UCr_4C_4$-type.

In at least one embodiment, the first phosphor is a phosphor doped with a dopant selected from the group of the following dopants: $Ce^{3+}$, $Eu^{2+}$, $Eu^{3+}$, $Yb^{2+}$, $Yb^{3+}$ or combinations thereof.

In at least one embodiment, the first phosphor has the following general formula: $M^*_{(1-z^*)}Z^*_{z^*}[A^*_{a^*}B^*_{b^*}C^*_{c^*}D^*_{d^*}E^*_{e^*}N_{4-n^*}O_{n^*}]$ where the elements and coefficients are as defined above, and where the phosphor is doped with a dopant selected from the group of the following dopants: $Eu^{3+}$, $Eu^{2+}$, $Yb^{2+}$, $Yb^{3+}$ or combinations thereof.

In at least one embodiment, the first phosphor is a phosphor of the following general formula:

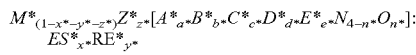

where the elements and coefficients are as defined above, and where further applies:
where $ES^* = Ce^{3+}$,
where RE* is selected from the group including $Eu^{2+}$, $Eu^{3+}$, $Yb^{2+}$ and $Yb^{3+}$.

In at least one embodiment, the conversion element is arranged in the beam pathway of the primary radiation. More particularly, the conversion element is arranged above a radiation exit surface of the semiconductor chip or the semiconductor laser. The radiation exit surface here is a main surface of the semiconductor chip or semiconductor laser or of the epitaxial layer sequence of the semiconductor chip or semiconductor laser. The radiation exit surface especially extends parallel to a main plane of extension of the semiconductor layers of the layer sequence, for example at least 85% or 90% of the radiation leaving the layer sequence via the radiation exit surface from the layer sequence.

The fact that a layer or an element is arranged or has been applied "to" or "over" another layer or another element may mean here and hereinafter that one layer or one element is arranged directly in direct mechanical and/or electrical and/or thermal contact on the other layer or the other element. Moreover, it can also mean that one layer or one element is arranged indirectly on or over the other layer or the other element. In this case, there may then be further layers and/or elements or a clear gap arranged between one layer or another or between one element and another.

In one embodiment, the semiconductor chip or semiconductor laser includes an active epitaxial layer sequence capable of emitting, in operation of the radiation-emitting optoelectronic component, a primary radiation in the UV region or blue region of the electromagnetic spectrum.

To generate the primary radiation, the epitaxial layer sequence may have, for example, a pn junction, a double heterostructure, a quantum well structure, or a multiple quantum well structure. The term "quantum well structure" does not include any statement as to dimensionality. It thus includes, inter alia, quantum wells, quantum wires, quantum dots and any combination of these structures. A semiconductor chip capable of emitting, in operation, UV primary radiation or primary radiation in the blue region of the electromagnetic spectrum is based, for example, on AlInGaN. For example, the semiconductor chip is based on $In_xAl_yGa_{1-x-y}N$ with $0 \le x \le 1$, $0 \le y \le 1$ and $x+y \le 1$.

The wavelength of the primary radiation can be shifted here by the composition, for example the ratio of indium to gallium in AlInGaN, into a predefined range for the respective application.

In at least one embodiment, the primary radiation is converted fully or virtually fully to the first secondary radiation. The component in this embodiment thus emits a total radiation that corresponds completely or virtually completely to the first secondary radiation and hence is in the green region of the electromagnetic spectrum. The fact that the total radiation corresponds virtually completely to the first secondary radiation means, that the total radiation is composed to an extent of more than 90%, especially to an extent of more than 95%, of the first secondary radiation. Particularly in the range from 475 nm to 500 nm inclusive, many leaf dyes such as carotenoids show a high absorption and can thus be efficiently stimulated by a component in this embodiment to photosynthesize on irradiation with the total radiation in the green region of the electromagnetic spectrum.

In at least one embodiment, the total radiation of the component is in the green region of the electromagnetic spectrum. In a non-limiting embodiment, the color point of the total radiation is in a color region which, in CIE color diagram (1931), is defined by the vertices $C_x/C_y=0.1/0.1$; 0.2/0.1; 0.225/0.24; 0.35/0.4 and 0.00817/0.547. A total radiation in this region can particularly efficiently stimulate plants to photosynthesize, such as land-based plants and water-based plants and microorganisms, as a result of which they have particularly rapid growth.

If the total radiation is in the green region of the electromagnetic spectrum, the conversion element or component may not include any further phosphor other than the first phosphor. Alternatively, it is possible that the conversion element includes a further phosphor that emits the primary radiation to a secondary radiation in the green region of the electromagnetic spectrum.

In at least one embodiment, the conversion element includes a second phosphor configured to convert the primary radiation at least partly to a second secondary radiation having a peak wavelength in the red region of the electromagnetic spectrum between 600 nm and 700 nm inclusive.

In at least one embodiment, the second phosphor is selected from the group including

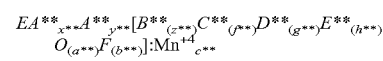

where A** is selected from the group including Li, Na, K, Rb, Cs, Cu, Ag, $NH_4$ or a combination thereof;
where EA** is selected from the group including Be, Mg, Ca, Ba, Sr, Zn or a combination thereof;
where B** is selected from the group including Si, Ge, Sn, Ti, Zr, Hf or a combination thereof;
where C** is selected from the group including Al, Ga, In, Gd, Y, Sc, La, Bi, Cr or a combination thereof;
where D** is selected from the group including Nb, Ta, V or a combination thereof;
where E** is selected from the group including W, Mo or a combination thereof;
where the partial charge d of $[EA^{}_{x^{}}A^{}_{y^{}}]^{d^{}}$ is calculated from (2x+y) and corresponds to the inverse of the partial charge e of $[[B^{}_{(z^{})}C^{}_{(f^{})}D^{}_{(g^{})}E^{}_{(h^{})}O_{(a^{})}F_{(b^{})}]:Mn^{+4}_{c^{}}]^{e^{}}$ which is composed of (4z+3f+5g+6h+4c−2a−b);
$(MgO)_{4-s}(MgF_2)_sGeO_2:Mn^{4+}$ $0 \le s \le 4$, such as s=0.5; the proportion of $Mn^{4+}$ may range between 0.01 mol % and 3 mol % inclusive, based on the molar amount of Mg, or alternatively may range between 0.01 mol % and 1 mol % inclusive, based on the molar amount of Mg;
$A'_2Ge_4O_9:Mn^{4+}$ or $A'_3A''Ge_8O_{18}:Mn^{4+}$, where A and A'=Li, Na, K and/or Rb;

M'$_{1-y'-z}$Z$_z$G$_g$(BE)$_b$(CE)$_c$(DE)$_d$E$_e$N$_{4-n}$O$_n$:(RE)$_{y'}$ where M'=Ca, Sr and/or Ba; Z=Na, K and/or Rb; G=Mg, Mn and/or Zn; BE=B, Al and/or Ga; CE=Si, Ge, Ti and/or Hf; DE=Li and/or Cu; E=P, V, Nb and/or Ta; RE=Eu and/or Yb; with 0≤y'≤0.2; 0≤z≤1; 0≤n≤0.5; 0≤g≤4, such as 2≤g≤3; 0≤b≤4; 0≤c≤4; 0≤d≤4; 0≤e≤4; g+b+c+d+e=4; and 2g+3b+4c+d+5e=10−y'−n+z, Sr$_2$SiN$_f$O$_{4-1.5f}$ with 0≤f≤8/3 and combinations thereof.

For the phosphor of the general formula

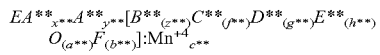

the individual elements and coefficients may be chosen such that the phosphor is a phosphor of the following narrower general formula:

(AE)$_x$[MF$_y$]:Mn$^{4+}$ where AE=Li, Na, K, Rb, Cs and/or NH$_4$, M=Si, Ge, Sn, Ti, Zr, Al, Ga, In, Sc, Y, La, Nb, Ta, Bi and/or Gd, x corresponds to the absolute value of charge of [MF$_y$] and y=5, 6 or 7.

Rather than

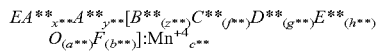

the second phosphor here and hereinafter may also be (AE)$_x$[MF$_y$]:Mn$^{4+}$ where: AE=Li, Na, K, Rb, Cs and/or NH$_4$, M=Si, Ge, Sn, Ti, Zr, Al, Ga, In, Sc, Y, La, Nb, Ta, Bi and/or Gd, x corresponds to the absolute value of the charge of [MF$_y$] and y=5, 6 or 7.

In one embodiment, a second phosphor of the formula (MgO)$_{4-s}$(MgF$_2$)$_s$GeO$_2$:Mn$^{4+}$ may have the formula Mg$_4$GeO$_{5.5}$F.

In one embodiment, a second phosphor of the formula A'$_2$Ge$_4$O$_9$:Mn$^{4+}$ or A'$_3$A"Ge$_8$O$_{18}$:Mn$^{4+}$ may have the formula K$_2$Ge$_4$O$_9$:Mn$^{4+}$; Rb$_2$Ge$_4$O$_9$:Mn$^{4+}$ or Li$_3$RbGe$_8$O$_{18}$:Mn$^{4+}$.

In one embodiment, a second phosphor of the formula M'$_{1-y'-z}$Z$_z$G$_g$(BE)$_b$(CE)$_c$(DE)$_d$E$_e$N$_{4-n}$O$_n$:(RE)$_{y'}$ may have the formula Sr[LiAl$_3$N$_4$]:Eu$^{2+}$ or Sr[LiAl$_3$N$_4$]:Yb$^{2+}$.

In at least one embodiment, the second phosphor is selected from the group including (Ca,Sr)AlSiN$_3$:Eu$^{2+}$, (Ca,Sr)AlSiN$_3$:Yb$^{2+}$; (Sr,Ca)$_3$Al$_2$O$_3$:Eu$^{2+}$; (Sr,Ca,Ba)$_2$Si$_5$N$_8$:Eu$^{2+}$; SrSiN$_2$:Eu$^{2+}$; SrAlSi$_4$N$_7$:Eu$^{2+}$; Ca$_5$Si$_2$Al$_2$N$_8$:Eu$^{2+}$; CaS:Eu$^{2+}$; Sr[LiAl$_3$N$_4$]:Eu$^{2+}$; Sr[LiAl$_3$N$_4$]:Yb$^{2+}$; K$_2$Ge$_4$O$_9$:Mn$^{4+}$; Rb$_2$Ge$_4$O$_9$:Mn$^{4+}$; Li$_3$RbGe$_8$O$_{18}$:Mn$^{4+}$; Sr$_4$Al$_{14}$O$_{25}$:Mn$^{4+}$; Mg$_2$TiO$_4$:Mn$^{4+}$; CaZrO$_3$:Mn$^{4+}$; Gd$_3$Ga$_5$O$_{12}$:Mn$^{4+}$; Al$_2$O$_3$:Mn$^{4+}$; GdAlO$_3$:Mn$^{4+}$; LaAlO$_3$:Mn$^{4+}$; LiAl$_5$O$_8$:Mn$^{4+}$; SrTiO$_3$:Mn$^{4+}$; Y$_2$Ti$_2$O$_7$:Mn$^{4+}$; Y$_2$Sn$_2$O$_7$:Mn$^{4+}$; CaAl$_{12}$O$_{19}$:Mn$^{4+}$; MgO:Mn$^{4+}$; Ba$_2$LaNbO$_6$:Mn$^{4+}$; K$_2$SiF$_6$:Mn$^{4+}$; Na$_2$SiF$_6$:Mn$^{4+}$; K$_2$TiF$_6$:Mn$^{4+}$; Mg$_4$GeO$_{5.5}$F:Mn$^{4+}$ and combinations thereof. More particularly, the position of the peak wavelength of the second phosphors can be influenced by the concentration of Eu$^{2+}$, Yb$^{2+}$ or Mn$^{4+}$.

In at least one embodiment, the primary radiation is converted partly to the first and second secondary radiations and the component emits a white total radiation. In this embodiment, the white total radiation results from the superposition of the primary radiation and the first and second secondary radiations. Preference is given here to a combination of a first phosphor of the formula BaSi$_2$N$_2$O$_2$:Eu$^{2+}$ with a second phosphor of the formula Sr[LiAl$_3$N$_4$]:Eu$^{2+}$, of a first phosphor of the formula BaSi$_4$Al$_3$N$_9$:Eu$^{2+}$ with a second phosphor of the formula Mg$_4$GeO$_{5.5}$F:Mn$^{4+}$, of a first phosphor of the formula BaSi$_4$Al$_3$N$_9$:Eu$^{2+}$ with a second phosphor of the formula K$_2$SiF$_6$:Mn$^{4+}$, of a first phosphor of the formula ALi$_3$XO$_4$:Eu$^{2+}$, such as having the formula A$_2$Li$_6$Si$_2$O$_8$:Eu$^{2+}$, with a second phosphor of the formula K$_2$SiF$_6$:Mn$^{4+}$, or of a first phosphor of the formula SrSiAl$_2$O$_3$N$_2$:Eu$^{2+}$ with a second phosphor of the formula K$_2$SiF$_6$:Mn$^{4+}$. Particular preference is given here to a combination of a first phosphor of the formula BaSi$_2$N$_2$O$_2$:Eu$^{2+}$ with a second phosphor of the formula Sr[LiAl$_3$N$_4$]:Eu$^{2+}$, of a first phosphor of the formula BaSi$_4$Al$_3$N$_9$:Eu$^{2+}$ with a second phosphor of the formula Mg$_4$GeO$_{5.5}$F:Mn$^{4+}$, of a first phosphor of the formula BaSi$_4$Al$_3$N$_9$:Eu$^{2+}$ with a second phosphor of the formula K$_2$SiF$_6$:Mn$^{4+}$, or of a first phosphor of the formula SrSiAl$_2$O$_3$N$_2$:Eu$^{2+}$ with a second phosphor of the formula K$_2$SiF$_6$:Mn$^{4+}$. The total radiation from such components has been found to be particularly efficient with regard to the promotion of plant growth or the promotion of growth of microorganisms.

In at least one embodiment, the conversion element includes one or more further phosphors that convert the primary radiation to a second radiation in the green or red region of the electromagnetic spectrum. The further phosphors may thus be present in the conversion element in addition to the first phosphor or the first and second phosphors.

In at least one embodiment, the further phosphor is selected from the group including Ce$^{3+}$-doped garnets, Eu$^{2+}$-doped nitrides, Ce$^{3+}$-doped nitrides, Eu$^{2+}$-doped oxynitrides, Eu$^{2+}$-doped sulfides, Eu$^{2+}$-doped α- and β-SiAlONs, Eu$^{2+}$-doped nitridoorthosilicates, Eu$^{2+}$-doped orthosilicates, Eu$^{2+}$-doped chlorosilicates, Eu$^{2+}$-doped chlorophosphates, Eu$^{2+}$-doped aluminates, Eu$^{2+}$-doped halophosphates and combinations thereof.

In one embodiment, the Ce$^{3+}$-doped garnet phosphor may have the formula (Y,Lu,Gd,Tb)$_3$(Al$_{1-x}$,Ga$_x$)$_5$O$_{12}$:Ce$^{3+}$. For example, the phosphor is Y$_3$Al$_5$O$_{12}$:Ce$^{3+}$ or Lu$_3$Al$_5$O$_{12}$:C$^{3+}$.

In one embodiment, the Eu$^{2+}$-doped nitride phosphor may have the formula (Ca,Sr)AlSiN$_3$:Eu$^{2+}$, Sr(Ca,Sr)Si$_2$Al$_2$N$_6$:Eu$^{2+}$ or (Ca,Ba,Sr)$_2$Si$_5$N$_8$:Eu$^{2+}$.

In one embodiment, the Eu$^{2+}$-doped oxynitride phosphor may have the formula (Sr,Ca)AlSiN$_3$*Si$_2$N$_2$O:Eu$^{2+}$ or (Ba,Sr,Ca)Si$_2$O$_2$N$_2$:Eu$^{2+}$.

In one embodiment, the Ce$^{3+}$-doped nitride phosphor may have the formula (Ca,Sr)Al$_{(1-4x/3)}$Si$_{(1+x)}$N$_3$:Ce$^{3+}$ with x=0.2-0.5.

In one embodiment, an Eu$^{2+}$-doped orthosilicate may have the formula (Ba,Sr,Ca)$_2$SiO$_4$:Eu$^{2+}$.

An Eu$^{2+}$-doped nitridoorthosilicate here may, for example, have the formula AE*$_{2-x-a}$RE$_x$Eu$_a$Si$_{1-y}$O$_{4-x-2y}$N$_x$ where AE*=Sr, Ba, Ca and/or Mg and RE is at least one rare earth metal, for example Eu. Moreover: 0<x≤0.1, such as 0.003≤x≤0.02 and 0<a≤0.2, alternatively 0.02≤a≤0.15 and 0≤y≤0.5. In a non-limiting embodiment, EA contains at least Sr and Ba; alternatively, EA contains at least Sr and Ba where 0.5≤Ba: Sr≤2, or alternatively 0.75≤Ba: Sr≤1.25.

In one embodiment, an Eu$^{2+}$-doped chlorosilicate may have the formula Ca$_8$Mg(SiO$_4$)$_4$O$_2$:Eu$^{2+}$.

In one embodiment, an Eu$^{2+}$-doped β-sialon may be an oxynitride or nitride that crystallizes in the same crystal structure as β-Si$_3$N$_4$, into which a rare earth metal has additionally been incorporated in the form of a solid solution. In a non-limiting embodiment, the β-sialon conforms to the general formula Si$_{6-z}$Al$_z$O$_z$N$_{8-z}$:RE or Si$_{6-x}$Al$_z$O$_y$N$_{8-y}$:RE$_z$, with 0<x≤4, 0≤y≥4, 0<z<1 and RE at least one rare earth metal. In a non-limiting embodiment, RE is Eu$^{2+}$ and/or Yb$^{2+}$.

An Eu$^{2+}$-doped aluminate has, for example, the formula BaMgAl$_{10}$O$_{17}$:Eu$^{2+}$.

An Eu$^{2+}$-doped halophosphate or chlorophosphate has, for example, the formula Sr$_5$(PO$_4$)$_3$Cl:Eu$^{2+}$ (SCAP for short).

In one embodiment, further phosphors used may be $Mn^{2+}$-doped phosphors. $Mn^{2+}$-doped phosphors used may especially be $(Sr,Ca,Ba,Mg)_2Si_5N_8:Mn^{2+}$; $BaMg_{(1-x)}Mn(II)_xAl_{10}O_{17}$ with $0<x\leq1$; $(Ba,Ca)ZnOS:Mn^{2+}$; $ZnGeN_2:Mn^{2+}$ or $\gamma$-$AlON:Mn^{2+}$.

In one embodiment, further phosphors used may be semiconductor nanoparticles. The semiconductor nanoparticles may be formed here, for example, from CdS, CdSe, CdTe, ZnS, ZnSe, ZnTe, HgTe, HgSe, GaP, GaAs, GaSb, AlP, AlAs, AlSb, InP, InAs, InSb, SiC, InN, AlN or solid solutions or combinations of the semiconductor materials mentioned. The solid solutions may, for example, be ternary or quaternary solid solutions.

In at least one embodiment, the spectrum of the white total radiation has at least three and at most five, such as three, intensity maxima in the range from 400 nm to 800 nm inclusive. The intensity maxima include the peak wavelengths of the semiconductor chip or the semiconductor laser and the peak wavelengths of the first phosphor, the second phosphor and optionally a further phosphor, and hence the main peaks of the semiconductor chip or the semiconductor laser and the main peaks of the first phosphor, the second phosphor and optionally a further phosphor. In addition, the intensity maxima, based on the peak wavelengths, include relative intensity maxima having an intensity of more than 65% of the intensity of the peak wavelengths, and hence peaks having an intensity of more than 65% based on the main peaks. The definition of an intensity maxima thus does not cover peaks having an intensity of below 65% based on the main peaks.

In at least one embodiment, at least one intensity maximum is in the range from 400 nm to 475 nm inclusive, at least one in the range from 475 nm to 500 nm inclusive, and at least one in the range from 600 nm to 700 nm inclusive. In a non-limiting embodiment, one intensity maximum is in the range from 400 nm to 475 nm inclusive, one in the range from 475 nm to 500 nm inclusive, and one in the range from 600 nm to 700 nm inclusive. In a non-limiting embodiment, the intensity maxima may include the peak wavelengths of the semiconductor chip or the semiconductor laser and the peak wavelengths of the first phosphor and the second phosphor.

In at least one embodiment, there is no intensity maximum in the range from 500 to 600 nm. This is particularly preferable in the present context since leaf dyes barely absorb, if at all, in this region and hence barely contribute, if at all, to promotion of plant growth. Advantageously, the component thus generates a total radiation which is white and very energy-efficient with regard to the illumination and growth of plants and/or microorganisms.

In at least one embodiment, the color point of the white total radiation is in a color region which, in the CIE diagram, lies on a line of the blackbody radiator or with a deviation from the line of the blackbody radiator of up to $\pm 0.02$ $C_x$ and/or $\pm 0.02$ $C_y$, such as $\pm 0.015$ $C_x$ and/or $\pm 0.015$ $C_y$.

In at least one embodiment, the color temperature of the white total radiation lies between 30 000 K and 2700 K inclusive, such as between 20 000 K and 3500 K inclusive.

In at least one embodiment, the spectrum of the white total radiation of the component fulfills the criterion that more than 60%, such as more than 75%, or alternatively more than 95%, of the photons emitted by the radiation-emitting optoelectronic component are within a wavelength range in which the superposition of the absorption of the leaf dyes chlorophyll A and chlorophyll B and carotenoid has a high absorption.

A high absorption is understood to mean an absorption of at least 10%, such as 20%, 25%, 30% or 50%, of the absorbance based on the maximum absorption in the range from 400 nm to 800 nm. The absorption spectra of chlorophyll A and chlorophyll B and $\beta$-carotene are shown in FIG. 10 (Ustin et al., Remote Sensing of Environment 113, Supplemental 1, 2009, S67-S77).

In at least one embodiment, more than 60%, such as more than 75%, or alternatively more than 95%, of the photons emitted by the component are within a wavelength range in which the absorption of the leaf dyes of a green alga has a high absorption. A reference spectrum used for the absorption of the leaf dyes of a green alga may, for example, be the absorption spectrum of Scenedesmos Acutos shown in FIG. 11 (Zeinalov et al., Bulg. J. Plant Physiol., 2000, 26(1-2), 58-59).

In one embodiment, the component includes a further semiconductor chip or semiconductor laser which, in operation of the component, emits a primary radiation in the red region of the electromagnetic spectrum. The peak wavelength may range from 600 nm to 700 nm inclusive. The conversion element includes a first phosphor configured to at least partly convert the primary radiation to a first secondary radiation having a peak wavelength in the green region of the electromagnetic spectrum between 475 nm and 500 nm inclusive and the first phosphor is selected from a group including $BaSi_4Al_3N_9$, $SrSiAl_2O_3N_2$, $BaSi_2N_2O_2$, $ALi_3XO_4$, $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ and combinations thereof, where A is at least one element selected from the group consisting of Li, Na, K, Rb, Cs and combinations thereof, where X is at least one element selected from the group consisting of Si, Ge, Ti, Zr, Hf and combinations thereof;

where M* is selected from the group including Ca, Sr, Ba and combinations thereof, where Z* is selected from the group including Na, K, Rb, Cs, Ag and combinations thereof, where A* is selected from the group including Mg, Mn, Zn and combinations thereof, where B* is selected from the group including B, Al, Ga and combinations thereof, where C* is selected from the group including Si, Ge, Ti, Zr, Hf and combinations thereof, where D* is selected from the group including Li, Cu and combinations thereof, where E* is selected from the group including P, V, Nb, Ta and combinations thereof, and where:

$0\leq x^*\leq 0.2;$ $0\leq y^*\leq 0.2;$ $0\leq x^*+y^*\leq 0.4;$ $0\leq z^*<1,$ $0\leq n^*\leq 4;$ $0\leq a^*\leq 4;$ $0\leq b^*\leq 4;$ $0\leq c^*\leq 4;$ $0\leq d^*\leq 4;$ $0\leq e^*\leq 4;$ $a^*+b^*+c^*+d^*+e^*=4;$ $2a^*+3b^*+4c^*+d^*+5e^*=10y^*-n^*+z^*;$ where $BaSi_4Al_3N_9$, $SrSiAl_2O_3N_2$, $BaSi_2N_2O_2$, $ALi_3XO_4$ and
$M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ may each independently be doped with a rare earth element.

In this embodiment, the component is configured to emit a white total radiation.

For example, $ALi_3XO_4$ is $A_2Li_6Si_2O_8$.

A further semiconductor chip or semiconductor laser which, in operation of the component, emits a primary radiation in the red region of the electromagnetic spectrum is based, for example, on InGaAlP. For example, the further semiconductor chip is based on $In_xAl_yGa_{1-x-y}P$ with $0≤x≤1$, $0≤y≤1$ and $x+y≤1$. The desired wavelength may be adjusted via the material composition.

In one embodiment, the component includes a further semiconductor chip or semiconductor laser which, in operation of the component, emits a primary radiation in the green region of the electromagnetic spectrum. In a non-limiting embodiment, the peak wavelength is in the range from 475 nm to 500 nm inclusive. The conversion element includes a second phosphor configured to at least partly convert the primary radiation to a second secondary radiation having a peak wavelength in the red region of the electromagnetic spectrum between 600 nm and 700 nm inclusive, and the second phosphor is selected from a group including

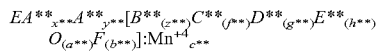

where A** is selected from the group including Li, Na, K, Rb, Cs, Cu, Ag, $NH_4$ or a combination thereof;
where EA** is selected from the group including Be, Mg, Ca, Ba, Sr, Zn or a combination thereof;
where B** is selected from the group including Si, Ge, Sn, Ti, Zr, Hf or a combination thereof;
where C** is selected from the group including Al, Ga, In, Gd, Y, Sc, La, Bi, Cr or a combination thereof;
where D** is selected from the group including Nb, Ta, V or a combination thereof;
where E** is selected from the group including W, Mo or a combination thereof;
where the partial charge d of $[EA^{}_{x^{}}A^{}_{y^{}}]^{d^{}}$ is calculated from $(2x^{}+y^{})$ and corresponds to the inverse of the partial charge e of $[[B^{}_{(z^{})}C^{}_{(f^{})}D^{}_{(g^{})}E^{}_{(h^{})}O_{(a^{})}F(b^{})]:Mn^+_{c^{}}]^{e^{}}$ which is composed of $(4z^{}+3f^{}+5g^{}+6h^{}+4c^{}-2a^{}-b^{})$;
$(MgO)_{4-s}(MgF_2)_sGeO_2:Mn^{4+}$ where $0≤s≤4$, such as s=0.5 $Mn^{4+}$ between 0.01 mol % and 3 mol % inclusive, or alternatively, based on the molar amount of Mg, between 0.01 mol % and 1 mol % inclusive, based on the molar amount of Mg;
$A'_2Ge_4O_9:Mn^{4+}$ or $A'_3A''Ge_8O_{18}:Mn^{4+}$, where A and A'=Li, Na, K and/or Rb;
$M'_{1-y'-z}Z_zG_g(BE)_b(CE)_c(DE)_dE_eN_{4-n}O_n:(RE)_{y'}$ where M'=Ca,Sr and/or Ba; Z=Na, K and/or Rb; G=Mg, Mn and/or Zn; BE=B, Al and/or Ga; CE=Si, Ge, Ti and/or Hf; DE=Li and/or Cu; E=P, V, Nb and/or Ta; RE=Eu and/or Yb; with $0≤y'≤0.2$; $0≤z≤1$; $0≤n≤0.5$; $0≤g≤4$, such as $2≤g≤3$; $0≤b≤4$; $0≤c≤4$; $0≤d≤4$; $0≤e≤4$; g+b+c+d+e=4; and 2g+3b+4c+d+5e=10-y'-n+z;
$Sr_2SiN_fO_{4-1.5f}$ where $0≤f≤8/3$ and combinations thereof.
In this embodiment, the component is configured to emit a white total radiation.
Rather than

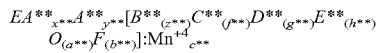

the second phosphor may also be $(AE)_x[MF_y]:Mn^{4+}$ where: AE=Li, Na, K, Rb, Cs and/or $NH_4$, M=Si, Ge, Sn, Ti, Zr, Al, Ga, In, Sc, Y, La, Nb, Ta, Bi and/or Gd, x corresponds to the absolute value of the charge of $[MF_y]$ and y=5, 6 or 7.

A further semiconductor chip or semiconductor laser which, in operation of the component, emits a primary radiation in the red region of the electromagnetic spectrum is based, for example, on AlInGaN or ZnO. For example, the semiconductor chip or semiconductor laser is based on $In_xAl_yGa_{1-x-y}N$ with $0≤x≤1$, $0≤y≤1$ and $x+y≤1$. Here too, the desired wavelength can be adjusted via the material composition.

In at least one embodiment, the peak wavelength of the semiconductor chip or semiconductor laser and the peak wavelength of the further semiconductor chip or further semiconductor laser differ by at least 25 nm.

In at least one embodiment, the phosphors are a powder. The powders may include particles, where the average particle size may range from 50 nm to 100 μm, or alternatively range from 2 to 35 μm.

In at least one embodiment, the conversion element includes a matrix material. The conversion element may consist of the first phosphor and the matrix material, of the first phosphor, a further phosphor that converts the primary radiation to a secondary radiation in the green region, and the matrix material, of the second phosphor and the matrix material, of the second phosphor and a further phosphor that converts the primary radiation to a secondary radiation in the red region, and the matrix material, of the first phosphor, the second phosphor and the matrix material, or of the first phosphor, the second phosphor, a further phosphor that converts the primary radiation to a secondary radiation in the green and/or red region and the matrix material. The phosphors here may be embedded in the matrix material. It is possible that the phosphors are distributed homogeneously in the matrix material. Alternatively, it is possible that the phosphors are distributed with a concentration gradient in the matrix material. The matrix material especially includes or consists of one of the following materials: a silicone, a glass, an epoxy resin.

One possible execution of the conversion element is the execution in the form of a casting, where the casting surrounds the semiconductor chip or semiconductor laser in a form-fitting manner. In addition, the casting that surrounds the semiconductor chip or semiconductor laser in a form-fitting manner may be stabilized at the side walls, for example by a housing, and is present, for example, in a recess of such a housing. If a further semiconductor chip or semiconductor laser is included in the component, this may also be surrounded in a form-fitting manner by the casting.

The conversion element may also be executed as a conversion layer. In the conversion layer, there is direct contact between conversion layer and the semiconductor chip or semiconductor laser, where the thickness of the conversion layer is, for example, less than the thickness of the semiconductor chip or semiconductor laser and, for example, may be constant at all radiation exit surfaces. Such a conversion layer is applied especially by the following methods: spray coating, injection molding, compression molding, jetting, dispensing or electrophoresis.

In one embodiment, the phosphors are present to an extent of 5% to 75% by weight, such as to an extent of 15% to 60% by weight, based on the total mass of phosphors and matrix material.

The conversion element may also assume the form of a sheet or film. The sheet or film is arranged above the semiconductor chip or semiconductor laser. In these further variants of execution of the conversion element, there is not necessarily direct and/or form-fitting contact of the conversion element with the semiconductor chip or the semiconductor laser. This means that a gap may exist between the conversion element and the semiconductor chip or semiconductor laser. In other words, the conversion element is downstream of the semiconductor chip or semiconductor laser and the primary radiation is incident thereon. An casting body or an air gap may then be formed between the conversion element and the semiconductor chip or semiconductor laser. What is advantageous about this geometric arrangement is that there is reduced heating of the conversion element by waste heat from the semiconductor chip or semiconductor laser particularly owing to the gap between the conversion element and the semiconductor chip or semiconductor laser.

In one embodiment, the conversion element consists of the first phosphor, of the first phosphor and a further phosphor that converts the primary radiation to a secondary radiation in the green region, of the second phosphor, of the second phosphor and a further phosphor that converts the primary radiation to a secondary radiation in the red region, of the first phosphor and the second phosphor, or of the first phosphor, the second phosphor and a further phosphor that converts the primary radiation to a secondary radiation in the green and/or red region. For example, this may be a ceramic of the phosphors. For example, in the embodiment of the conversion element as a sheet, it is a sheet consisting of a ceramic of the phosphors.

For example, the radiation-emitting optoelectronic component may be a light-emitting diode (LED).

The specified embodiments of the radiation-emitting optoelectronic component may be used for uses specified hereinafter. All features of the radiation-emitting optoelectronic component are also disclosed for the use thereof, and vice versa.

A use of the radiation-emitting optoelectronic component according to the abovementioned embodiment for illumination of plants, especially land-based plants and water-based plants, and microorganisms, especially microorganisms capable of photosynthesis, is specified. In at least one embodiment, the plants are stimulated to photosynthesize by the total radiation emitted by the radiation-emitting optoelectronic component.

In one embodiment, the total radiation emitted by the radiation-emitting optoelectronic component is absorbed by leaf dyes of the plants, especially by chlorophyll A, chlorophyll B, carotenoids, Scenedesmos Acutos, zeaxanthines, lycopenes and/or luteins, such as by chlorophyll A, chlorophyll B, carotenoids and/or Scenedesmos Acutos. The absorption of the total radiation corresponds here especially to the first step of photosynthesis in plants. It is thus possible to enhance plant growth by an increased rate of photosynthesis. Particularly in the case of use or of emission of a white total radiation, discoloration on the plant, for example as a result of fungi or deficiency phenomena, is apparent.

The leaf dyes mentioned absorb strongly in the range from 400 nm to 520 nm and 610 nm to 720 nm. As a result, these can particularly efficiently absorb a total radiation in the green region having a peak wavelength in the range from 475 nm to 500 nm inclusive or a white total radiation having a peak wavelength in the range from 475 nm to 500 nm inclusive and in the range from 600 nm to 700 nm inclusive. As a result, the radiation-emitting optoelectronic components are particularly suitable for increasing the rate of photosynthesis and hence promoting the growth of plants.

The radiation-emitting optoelectronic component may find use, for example, in greenhouses.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the illumination apparatus. In the following description, various aspects are described with reference to the following drawings, in which:

FIGS. 2A to 9A show emission spectra of various working non-limiting examples of radiation-emitting optoelectronic components, FIGS. 2B to 9B show how many percent of the photons emitted in the total radiation from a working example of a radiation-emitting optoelectronic component are within a range in which the absorption spectrum of a green alga has at least 10% intensity based on the maximum, FIGS. 2C, 4C, 6C, 7C, 8C and 9C show color points of the white total radiation from various working non-limiting examples of radiation-emitting optoelectronic components in the CIE color diagram (1931)

DETAILED DESCRIPTION

Figure 1A:
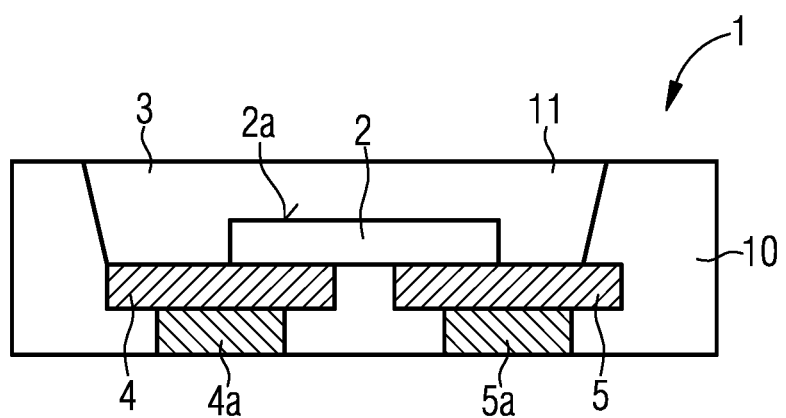
FIGS. 1A and 1B show schematic side views of various non-limiting embodiments of radiation-emitting optoelectronic components.

The working example of a radiation-emitting optoelectronic component 1 which is shown in FIG. 1A has a semiconductor chip 2 which, in operation, emits primary radiation in the UV region or blue region of the electromagnetic spectrum. The semiconductor chip 2 is based on aluminum indium gallium nitride. The semiconductor chip 2 is secured on a first contact 4 and a second contact 5 and electrically connected to these contacts. The contacts 4, 5 are electrically connected by vias 4a and 5a.

In the first working example shown in FIG. 1A, the first and second electrical contacts 4, 5 are embedded into an opaque, for example prefabricated, base housing 10 with a recess 11. "Prefabricated" is understood to mean that the base housing 10 has already been formed on the contacts 4, 5, for example by means of injection molding, before the semiconductor chip 2 is mounted onto the contacts 4, 5. The base housing 10 includes, for example, an opaque plastic, and the recess 11 may be coated with a reflective coating of the inner walls. The contacts 4, 5 are formed from a metal having a reflectivity for the primary and/or secondary radiation of greater than 60%, such as greater than 70%, or alternatively than 80%, for example silver or gold.

The conversion element 3 in the working example of FIG. 1A takes the form of an casting and fills the recess 11. The conversion element 3 here includes a silicone or an epoxy resin in which particles of a first phosphor and particles of a second phosphor are embedded. Preference is given here to a combination of a first phosphor of the formula $BaSi_2N_2O_2:Eu^{2+}$ with a second phosphor of the formula $Sr[LiAl_3N_4]:Eu^{2+}$, of a first phosphor of the formula $BaSi_4Al_3N_9:Eu^{2+}$ with a second phosphor of the formula $Mg_4GeO_{5.5}F:Mn^{4+}$, of a first phosphor of the formula $BaSi_4Al_3N_9:Eu^{2+}$ with a second phosphor of the formula $K_2SiF_6:Mn^{4+}$, of a first phosphor of the formula $A_2Li_6Si_2O_8:Eu^{2+}$ with a second phosphor of the formula $K_2SiF_6:Mn^{4+}$, or of a first phosphor of the formula $SrSiAl_2O_3N_2:Eu^{2+}$ with a second phosphor of the formula $K_2SiF_6:Mn^{4+}$. The first phosphor partly converts the primary radiation to a secondary radiation in the green region of the electromagnetic spectrum and the second phosphor partly converts the primary radiation to a secondary radiation in the red region of the electromagnetic spectrum. The total radiation from the component results from a superposition of the primary radiation and the secondary radiation and is white. In this working example, the total radiation is emitted upward via the conversion element 3.

Figure 1B:
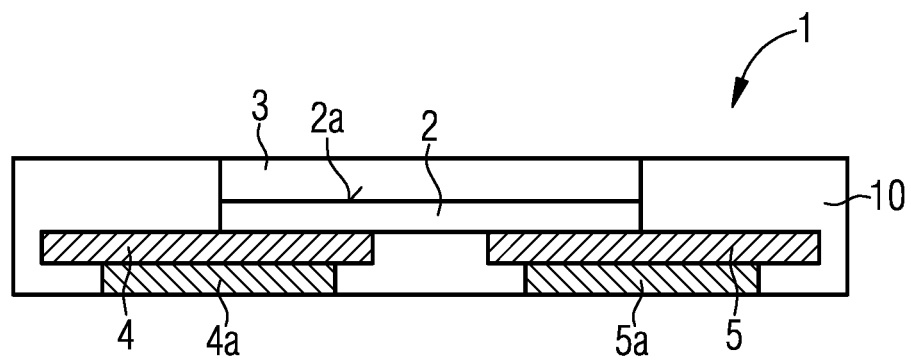

In the working example of a radiation-emitting optoelectronic component 1 shown in FIG. 1B, the conversion element 3, by contrast with the component in FIG. 1A, takes the form of one layer arranged above the semiconductor chip 2. The layer is arranged above the radiation exit surface of the semiconductor chip. It is possible that the layer covers the side walls of the semiconductor chip (not shown here).

In each of FIGS. 2A to 9A, the wavelength λ, in nm is plotted on the x axis and the relative intensity rI on the y axis.

In each of FIGS. 2B to 9B, the relative absorption of a green alga (rA) and the photons emitted within this range (P) in the total radiation from a radiation-emitting optoelectronic component are compared in percent.

FIGS. 2C and 4C and 6C to 9C each show a color point of the total radiation from a working example of a radiation-emitting optoelectronic component in the CIE 1931 color space, with the x fraction of the red base color ($C_x$) plotted on the x axis and the y fraction of the green base color ($C_y$) on the y axis. The differently hatched regions indicate the different color regions. The unhatched region in each case shows white color point within the CIE color space.

Figures 2A, 2B:
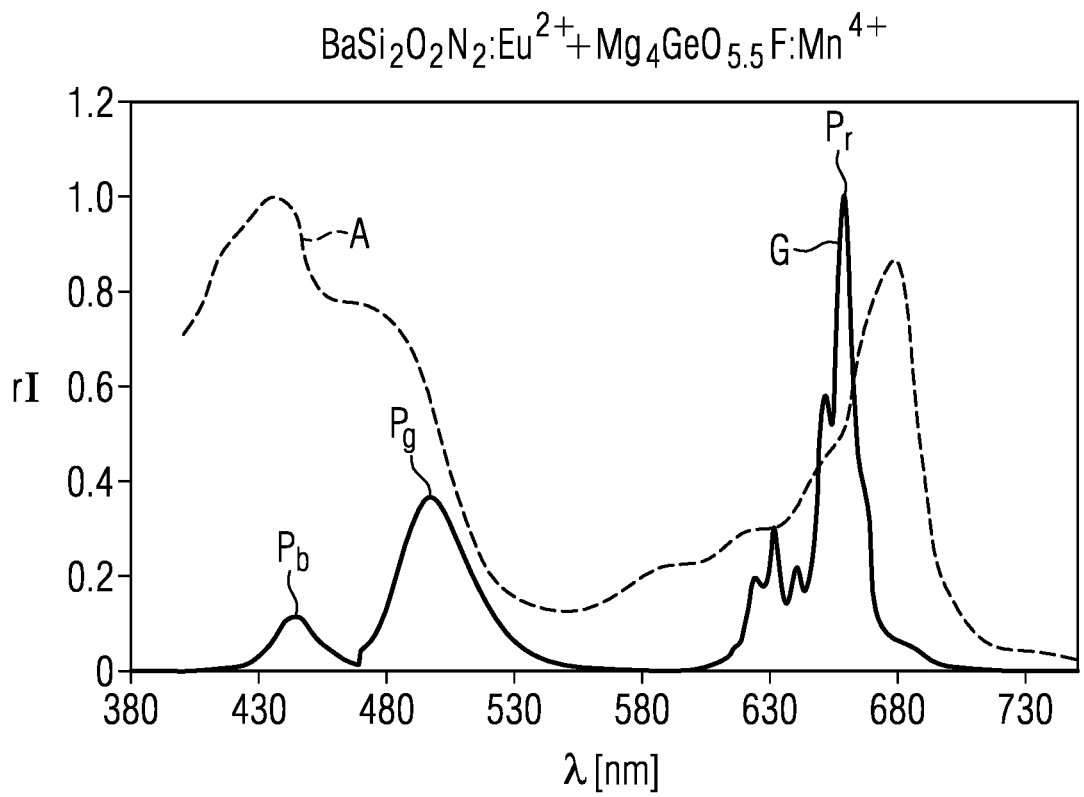

FIG. 2A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $BaSi_2O_2N_2:Eu^{2+}$ having a peak wavelength ($P_g$) in the range from 475 nm to 500 nm and a secondary radiation in the red region of a second phosphor of the formula $Mg_4GeO_{5.5}F:Mn^{4+}$ having a peak wavelength ($P_r$) in the range from 600 nm to 700 nm. The total radiation G is white overall. The color point of the total radiation in the CIE color diagram (1931) is at $C_x=0.323$ and $C_y=0.327$ (shown in FIG. 2C). The spectrum thus has three intensity maxima ($P_b$, $P_g$, $P_a$) in the range from 400 nm to 800 nm inclusive. There is one intensity maximum here in the range from 400 nm to 475 nm inclusive, one in the range from 475 nm to 500 nm inclusive, and one in the range from 600 nm to 700 nm inclusive.

Figure 2C:
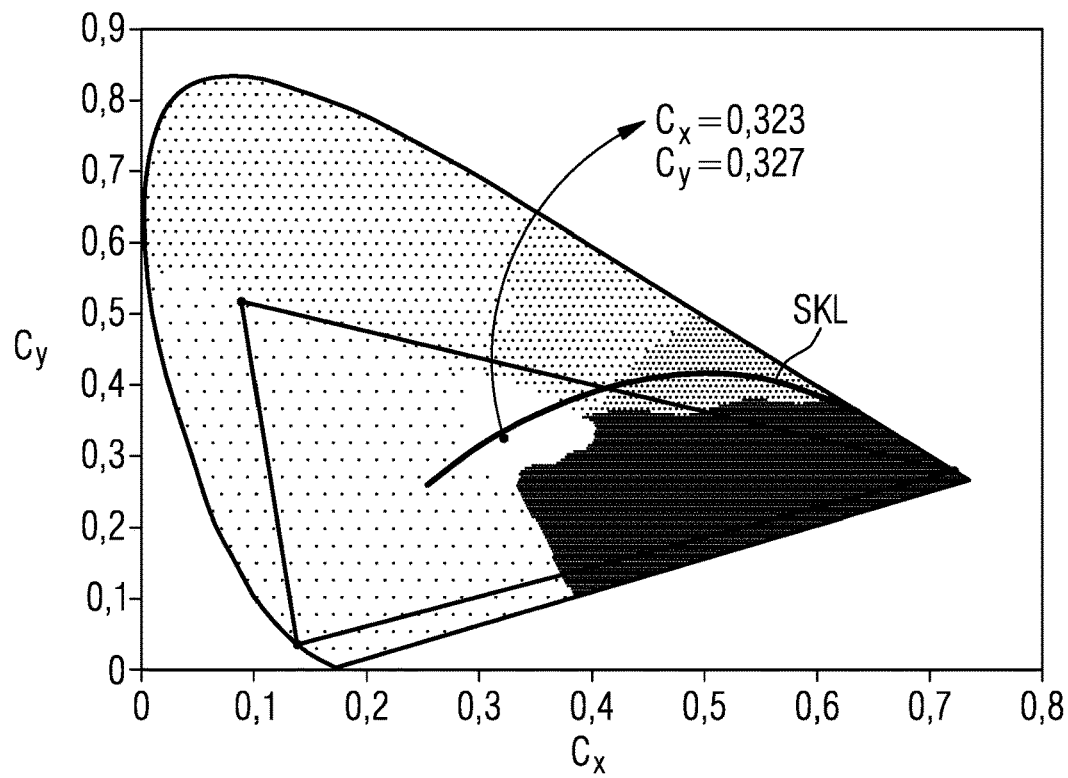

It is apparent from FIG. 2C that the color point of the white total radiation G is in a color region around the line of the blackbody radiator (SKL) with a deviation of up to ±0.02 $C_x$ and ±0.02 $C_y$.

It is apparent inter alia from FIG. 2B that 99% of the photons emitted in the total radiation G from the component are within a wavelength range in which the relative absorption of the leaf dye of a green alga is 0.1, i.e. 10%, based on the maximum absorption. The irradiation of green algae with the total radiation from the optoelectronic component in this embodiment can efficiently stimulate these to photosynthesize and hence to grow. The table shows further proportions of photons emitted by the component at relative absorbances of green algae.

Figure 3A:
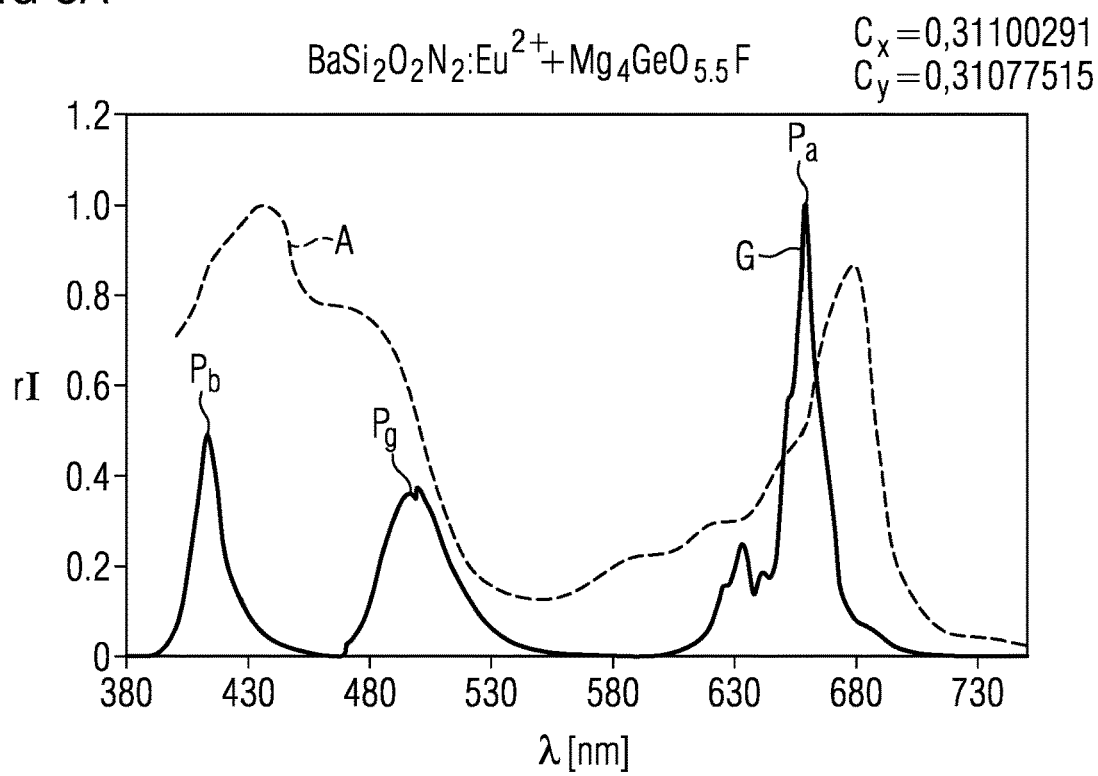

FIG. 3A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 420 nm, a secondary radiation in the green region of a first phosphor of the formula $BaSi_2O_2N_2:Eu^{2+}$ having a peak wavelength ($P_g$) in the range from 475 nm to 500 nm and a secondary radiation in the red region of a second phosphor of the formula $Mg_4GeO_{5.5}F:Mn^{4+}$ having a peak wavelength ($P_r$) in the range from 600 nm to 700 nm. The total radiation G is white overall. The color point of the total radiation in the CIE color diagram (1931) is at $C_x=0.311$ and $C_y=0.311$. The spectrum thus has three intensity maxima ($P_b$, $P_g$, $P_a$) in the range from 400 nm to 800 nm inclusive. There is one intensity maximum here in the range from 400 nm to 475 nm inclusive, one in the range from 475 nm to 500 nm inclusive, and one in the range from 600 nm to 700 nm inclusive.

Figures 3B, 4A:
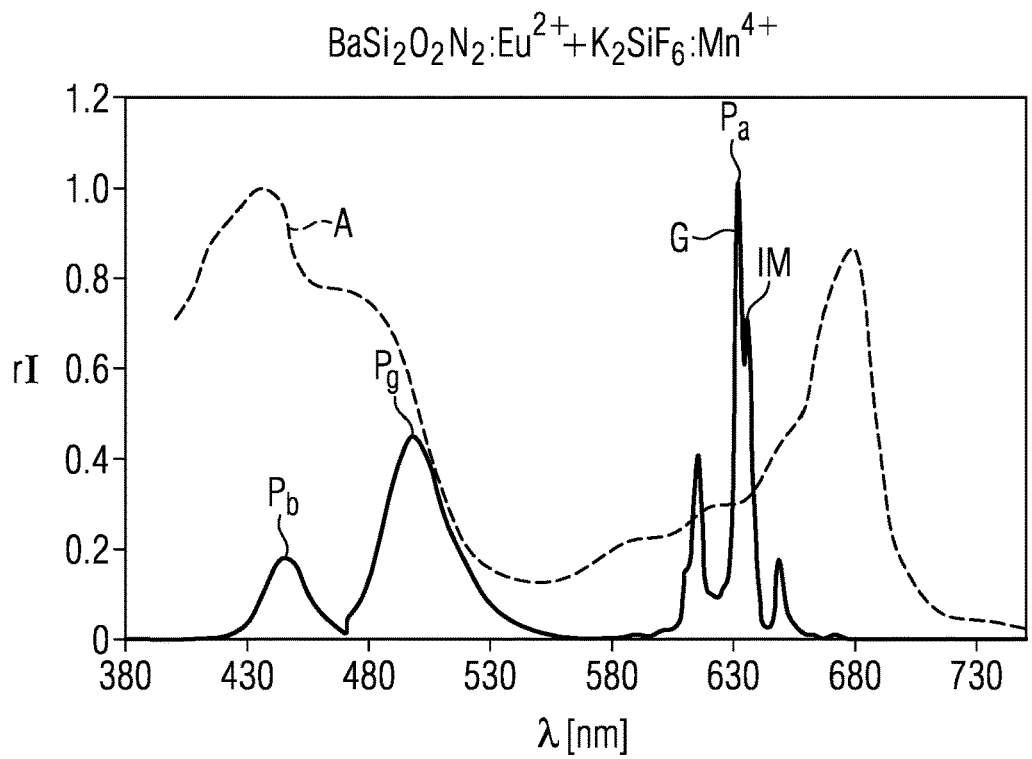

It is apparent inter alia from FIG. 3B that 99% of the photons emitted in the total radiation G from the component are within a wavelength range in which the relative absorption of the leaf dye of a green alga is 0.1, i.e. 10%, based on the maximum absorption. The irradiation of green algae with the total radiation from the optoelectronic component in this embodiment can efficiently stimulate these to photosynthesize and hence to grow.

FIG. 4A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $BaSi_2O_2N_2:Eu^{2+}$ having a peak wavelength ($P_g$) in the range from 475 nm to 500 nm, and a secondary radiation in the red region of a second phosphor of the formula $K_2SiF_6:Mn^{4+}$ having a peak wavelength ($P_r$) in the range from 600 nm to 700 nm. The spectrum has four intensity maximum. Three of the intensity maxima correspond to $P_b$, $P_g$ and $P_r$; the fourth is identified by IM. IM, based on the main peak having the peak wavelength $P_r$, is a relative intensity maximum having an intensity of more than 65% of the intensity of the peak wavelength $P_r$. There is thus one intensity maximum in the range from 400 nm to 475 nm inclusive, one intensity maximum in the range from 475 nm to 500 nm inclusive, and two intensity maxima in the range from 600 nm to 700 nm inclusive. The total radiation G is white overall. The color point of the total radiation in the CIE color diagram (1931) is at $C_x=0.314$ and $C_y=0.312$ (shown in FIG. 4C).

Figures 4B, 4C:
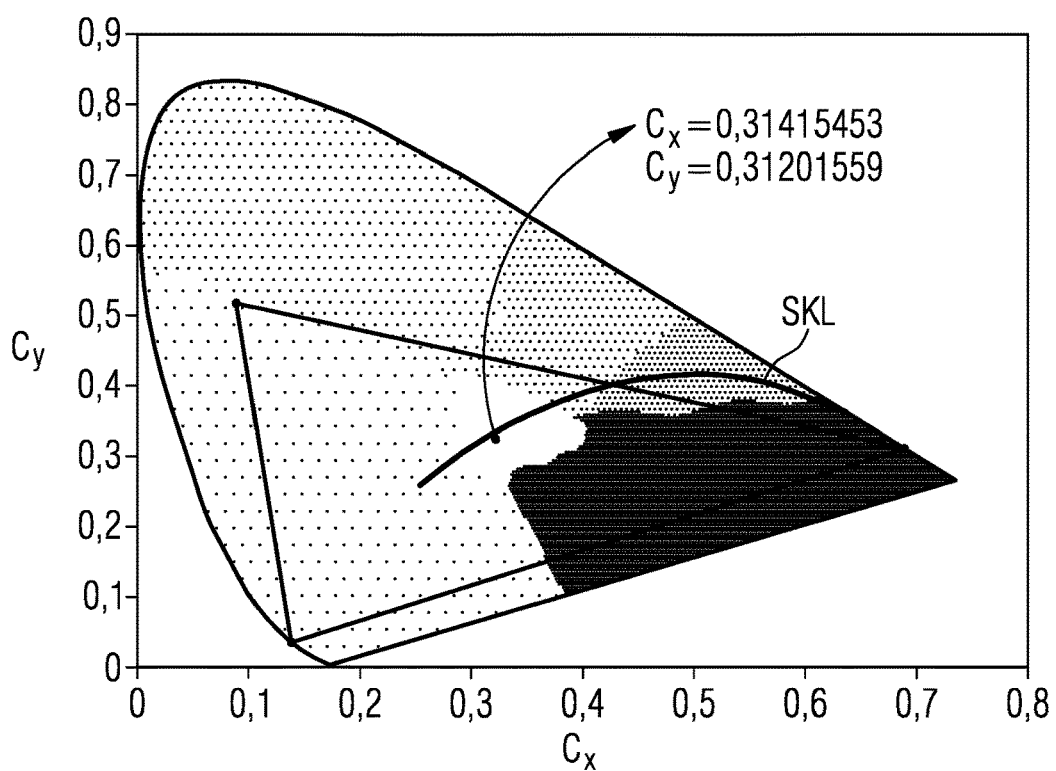

It is apparent from FIG. 4C that the color point of the white total radiation G is within a color region which is around the line of the blackbody radiator (SKL) with a deviation of up to ±0.02 $C_x$ and ±0.02 $C_y$.

It is apparent inter alia from FIG. 4B that 99% of the photons emitted in the total radiation G from the component are within a wavelength range in which the relative absorption of the leaf dye of a green alga is 0.1, i.e. 10%, based on the maximum absorption. The irradiation of green algae with the total radiation from the optoelectronic component in this embodiment can efficiently stimulate these to photosynthesize and hence to grow. The table shows further proportions of photons emitted by the component at relative absorbances of green algae.

Figures 5A, 5B:
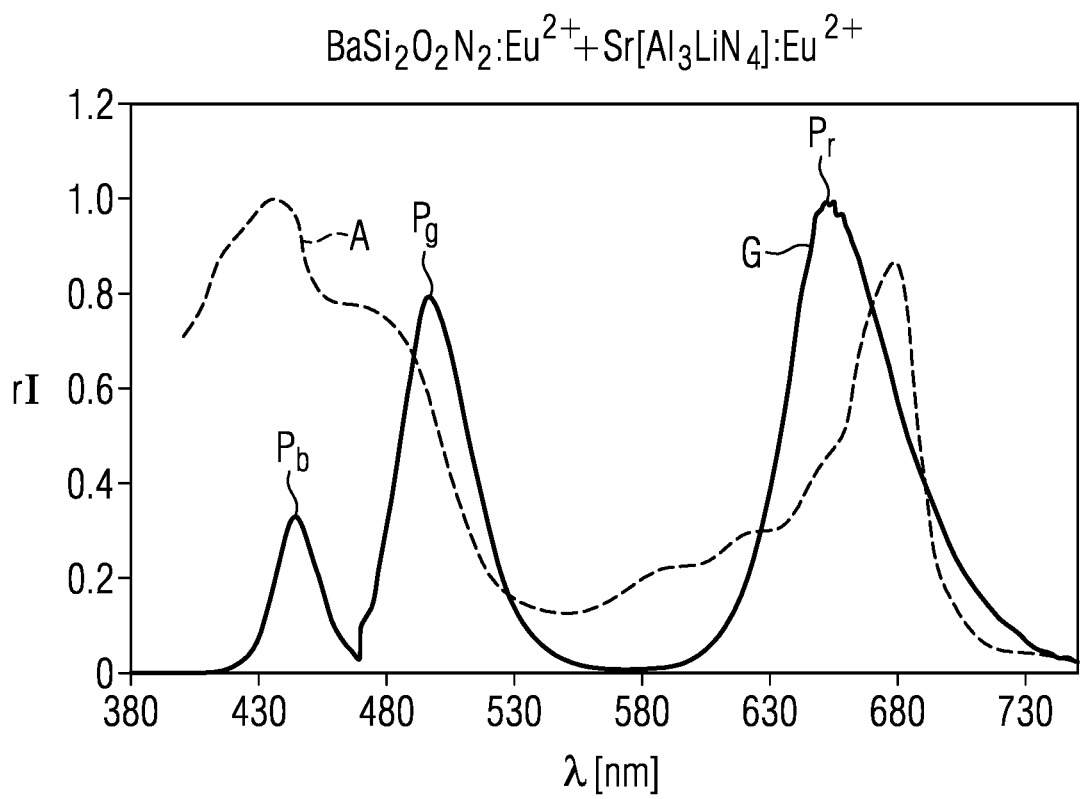

FIG. 5A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $BaSi_2O_2N_2:Eu^{2+}$ having a peak wavelength ($P_g$) in the range from 475 nm to 500 nm, and a secondary radiation in the red region of a second phosphor of the formula $Sr[Al_3LiN_4]:Eu^{2+}$ having a peak wavelength ($P_r$) in the range from 600 nm to 700 nm. The total radiation G is white overall. The spectrum thus has three intensity maxima ($P_b$, $P_g$, $P_a$) in the range from 400 nm to 800 nm inclusive. There is one intensity maximum here in the range from 400 nm to 475 nm inclusive, one in the range from 475 nm to 500 nm inclusive, and one in the range from 600 nm to 700 nm inclusive.

The table in FIG. 5B gives proportions of photons emitted in the total radiation from the component at relative absorbances of green algae. For example, 99% of the photons emitted in the total radiation G from the component are within a wavelength range in which the relative absorption of the leaf dye of a green alga is 0.1, i.e. 10%, based on the maximum absorption.

The irradiation of green algae with the total radiation from the optoelectronic component in this embodiment can efficiently stimulate these to photosynthesize and hence to grow.

Figures 6A, 6B:
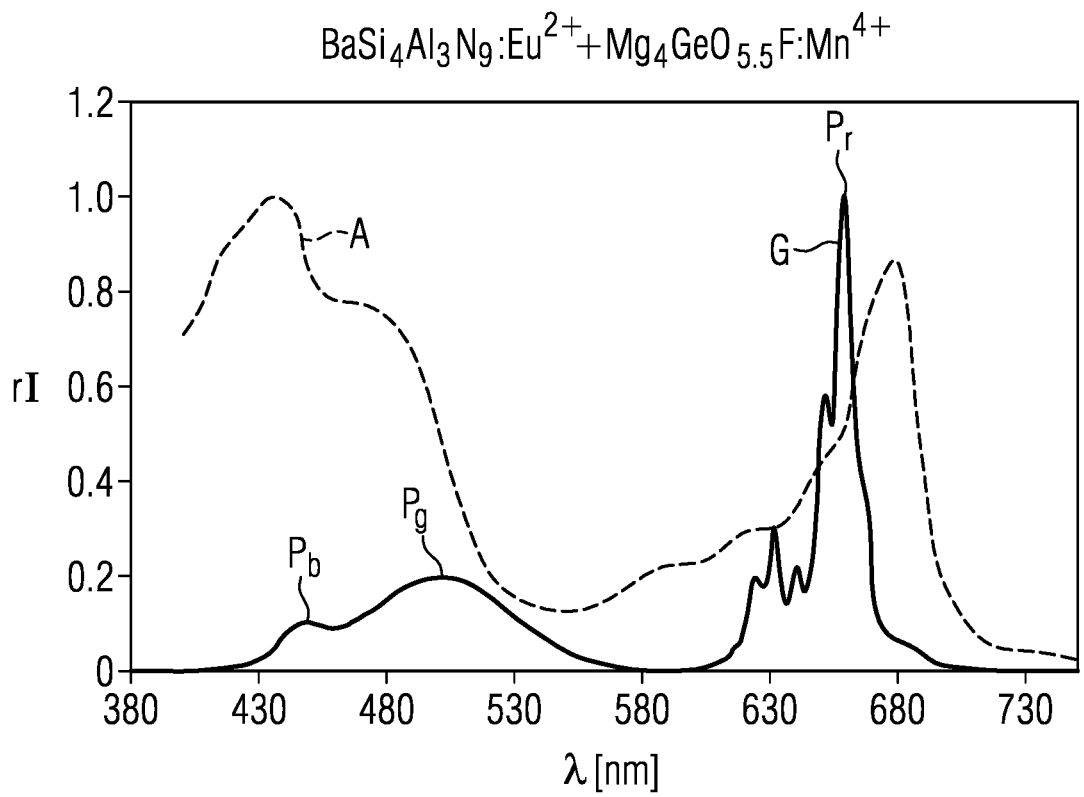

FIG. 6A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $BaSi_4Al_3N_9:Eu^{2+}$ having a peak wavelength ($P_g$) in the range from 475 nm to 500 nm, and a secondary radiation in the red region of a second phosphor of the formula $Mg_4GeO_{5.5}F:Mn^{4+}$ having a peak wavelength ($P_r$) in the range from 600 nm to 700 nm. The total radiation G is white overall. The color point of the total radiation in the CIE color diagram (1931) is at $C_x=0.316$ and $C_y=0.312$ (shown in FIG. 6C). The spectrum has three intensity maxima ($P_b$, $P_g$, $P_a$) in the range from 400 nm to 800 nm inclusive. There is one intensity maximum in the range from 400 nm to 475 nm inclusive, one in the range from 475 nm to 500 nm inclusive, and one in the range from 600 nm to 700 nm inclusive.

Figure 6C:
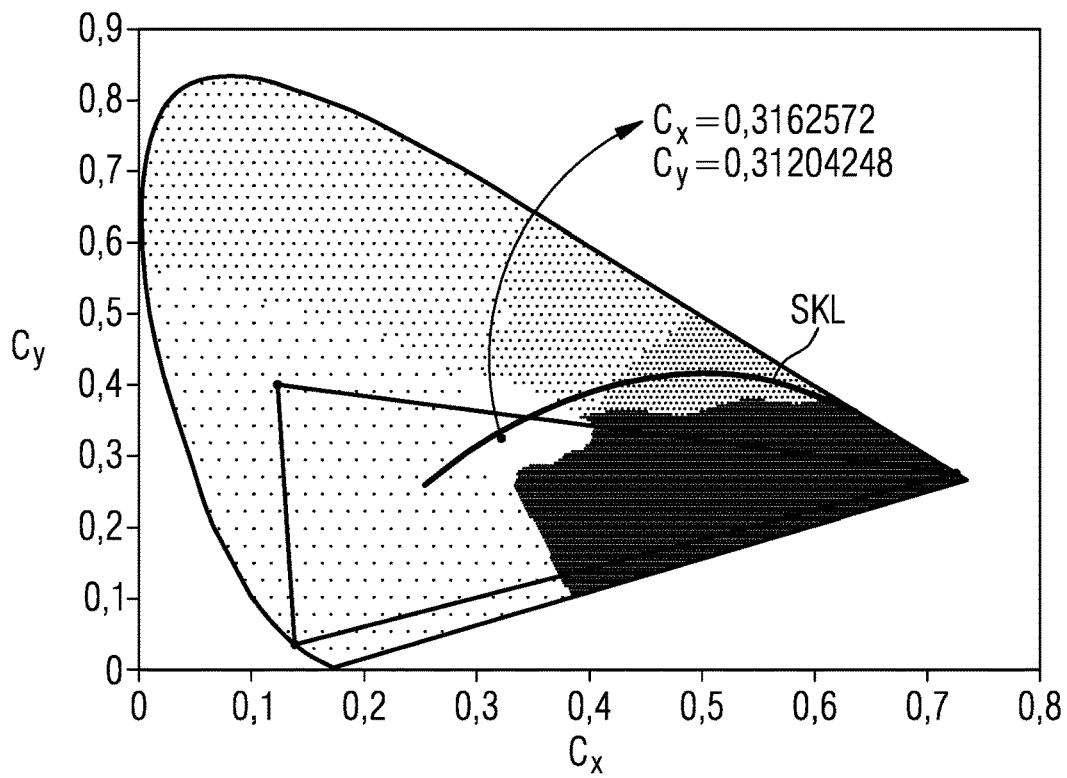

It is apparent from FIG. 6C that the color point of the white total radiation G is within a color region which is around the line of the blackbody radiator (SKL) with a deviation of up to ±0.02 $C_x$ and ±0.02 $C_y$.

The table in FIG. 6B gives proportions of photons emitted in the total radiation from the component at relative absorbances of green algae. For example, 68% of the photons emitted in the total radiation G from the component are within a wavelength range in which the relative absorption of the leaf dye of a green alga is 0.5, i.e. 50%, based on the maximum absorption. The irradiation of green algae with the total radiation from the optoelectronic component in this embodiment can efficiently stimulate these to photosynthesize and hence to grow.

Figure 7A:
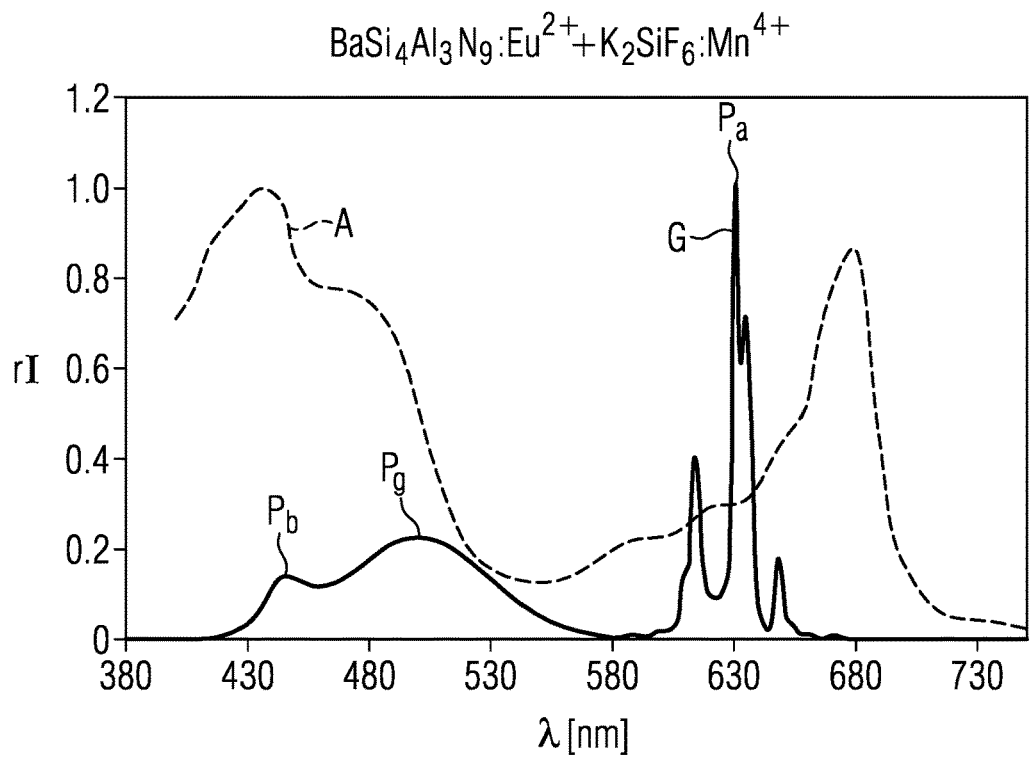

FIG. 7A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $BaSi_4Al_3N_9:Eu^{2+}$ having a peak wavelength ($P_g$) in the range from 475 nm to 500 nm, and a secondary radiation in the red region of a second phosphor of the formula $K_2SiF_6:Mn^{4+}$ having a peak wavelength ($P_r$) in the range from 600 nm to 700 nm. The total radiation G is white overall. The color point of the total radiation in the CIE color diagram (1931) is at $C_x=0.321$ and $C_y=0.308$ (shown in FIG. 7C). The spectrum thus has three intensity maxima ($P_b$, $P_g$, $P_a$) in the range from 400 nm to 800 nm inclusive. There is one intensity maximum here in the range from 400 nm to 485 nm inclusive, one in the range from 475 nm to 500 nm inclusive, and one in the range from 600 nm to 700 nm inclusive.

Figures 7B, 7C:
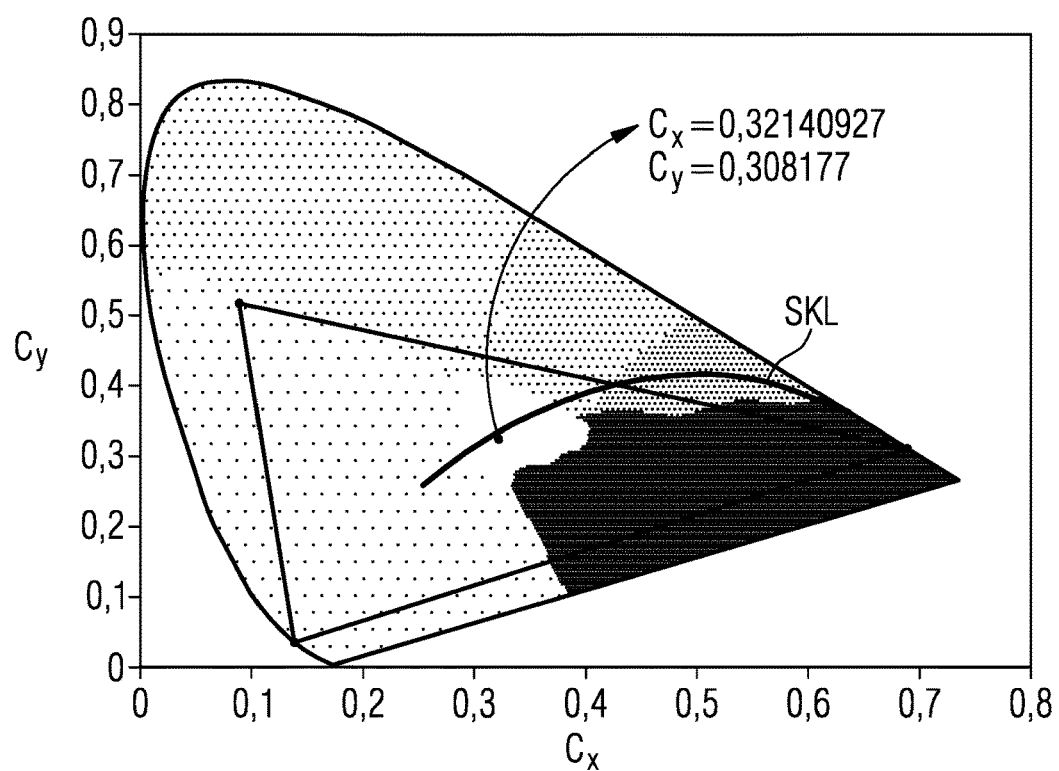

It is apparent from FIG. 7C that the color point of the white total radiation G is within a color region which is around the line of the blackbody radiator (SKL) with a deviation of up to ±0.02 $C_x$ and ±0.02 $C_y$.

The table in FIG. 7B gives proportions of photons emitted in the total radiation from the component at relative absorbances of green algae. For example, 93% of the photons emitted in the total radiation G from the component are within a wavelength range in which the relative absorption of the leaf dye of a green alga is 0.25, i.e. 25%, based on the maximum absorption.

The irradiation of green algae with the total radiation from the optoelectronic component in this embodiment can efficiently stimulate these to photosynthesize and hence to grow.

Figures 8A, 8B:
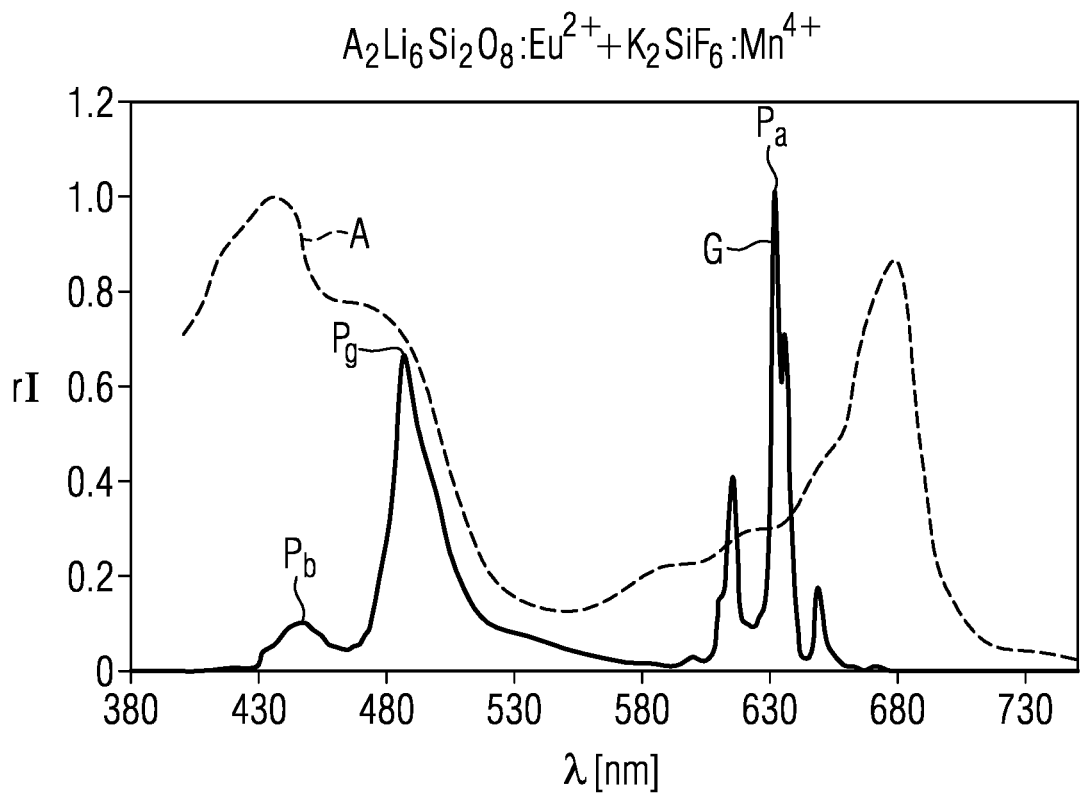

FIG. 8A gives a spectrum of the total radiation G from a working example of a radiation-emitting optoelectronic component. In addition, the diagram shows the absorption A of a green alga using the example of *Scenedesmus acutus*.

The total radiation G is composed of a primary radiation having a peak wavelength ($P_b$) of about 445 nm, a secondary radiation in the green region of a first phosphor of the formula $A_2Li_6Si_2O_8:Eu^{2+}$ having a peak wavelength ($P_g$) in the range from 475 nm to 500 nm, and a secondary radiation in the red region of a second phosphor of the formula $K_2SiF_6:Mn^{4+}$ having a peak wavelength ($P_r$) in the range from 600 nm to 700 nm. The first phosphor of FIG. 8 (wavelength range 470 to 500 nm) is specifically NaK$(Li_3SiO_4)_2:Eu^{2+}$. The total radiation G is white overall. The color point of the total radiation in the CIE color diagram (1931) is at $C_x=0.322$ and $C_y=0.310$ (shown in FIG. 8C). The spectrum thus has three intensity maxima ($P_b$, $P_g$, $P_a$) in the range from 400 nm to 800 nm inclusive. There is one intensity maximum here in the range from 400 nm to 475 nm inclusive, one in the range from 475 nm to 500 nm inclusive, and one in the range from 600 nm to 700 nm inclusive.

Figure 8C:
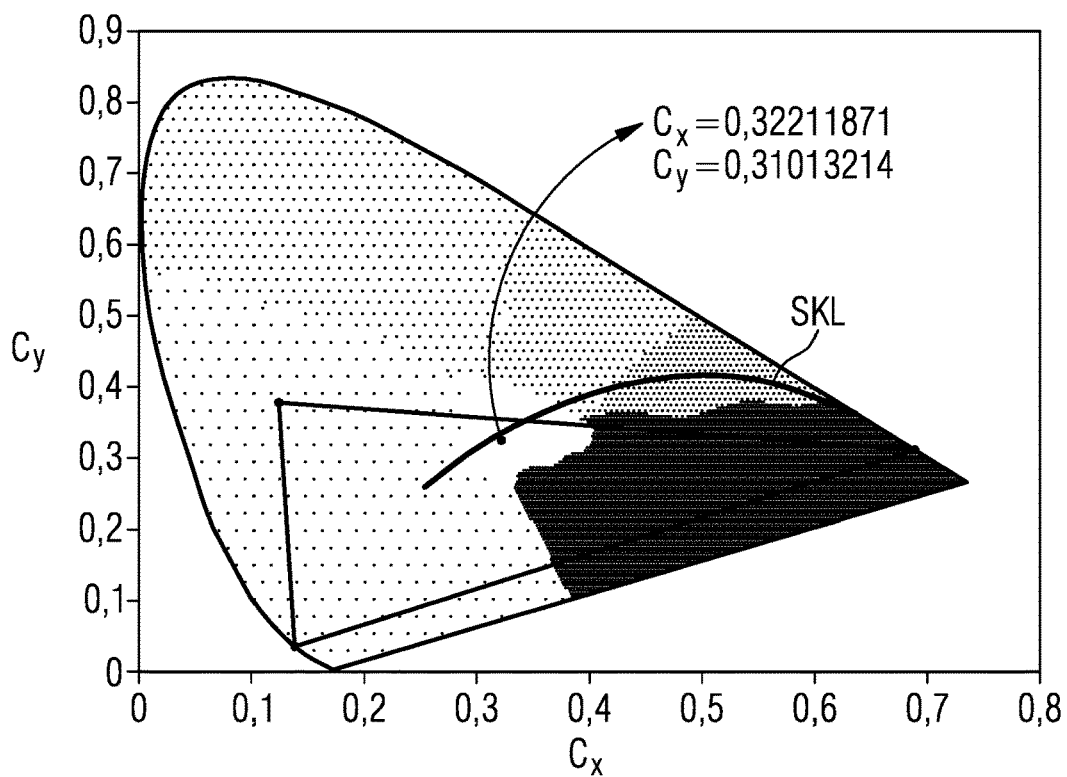

It is apparent from FIG. 8C that the color point of the white total radiation G is within a color region which is around the line of the blackbody radiator (SKL) with a deviation of up to ±0.02 $C_x$ and ±0.02 $C_y$.

The table in FIG. 8B gives proportions of photons emitted in the total radiation from the component at relative absorbances of green algae. For example, 89% of the photons emitted in the total radiation G from the component are within a wavelength range in which the relative absorption of the leaf dye of a green alga is 0.3, i.e. 30%, based on the maximum absorption. The irradiation of green algae with the total radiation from the optoelectronic component in this embodiment can efficiently stimulate these to photosynthesize and hence to grow.

Figure 9A:
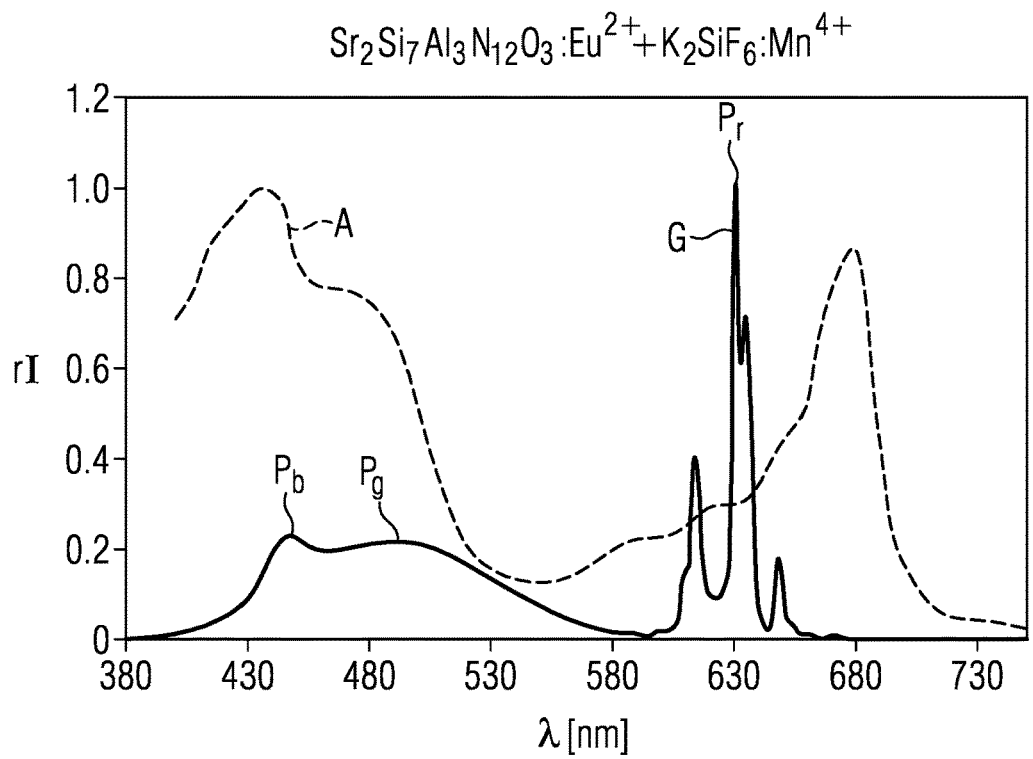

FIG. 9A gives a spectrum of the total radiation G from a working example of a radiation-emitting optoelectronic component. In addition, the diagram shows the absorption A of a green alga using the example of Scenedesmus acutus.

The total radiation G is composed of a primary radiation having a peak wavelength ($P_b$) of about 445 nm, a secondary radiation in the green region of a first phosphor of the formula SrSiAl$_2$O$_3$N$_2$:Eu$^{2+}$ having a peak wavelength ($P_g$) in the range from 475 nm to 500 nm, and a secondary radiation in the red region of a second phosphor of the formula K$_2$SiF$_6$:Mn$^{4+}$ having a peak wavelength ($P_r$) in the range from 600 nm to 700 nm. FIG. 9A thus shows the phosphors SrSiAl$_2$O$_3$N$_2$:Eu$^{2+}$+K$_2$SiF$_6$:Mn$^{4+}$. The total radiation G is white overall. The color point of the total radiation in the CIE color diagram (1931) is at $C_x$=0.294 and $C_y$=0.266 (shown in FIG. 9C). The spectrum thus has three intensity maxima ($P_b$, $P_g$, $P_a$) in the range from 400 nm to 800 nm inclusive. There is one intensity maximum here in the range from 400 nm to 475 nm inclusive, one in the range from 475 nm to 500 nm inclusive, and one in the range from 600 nm to 700 nm inclusive.

Figures 9B, 9C:
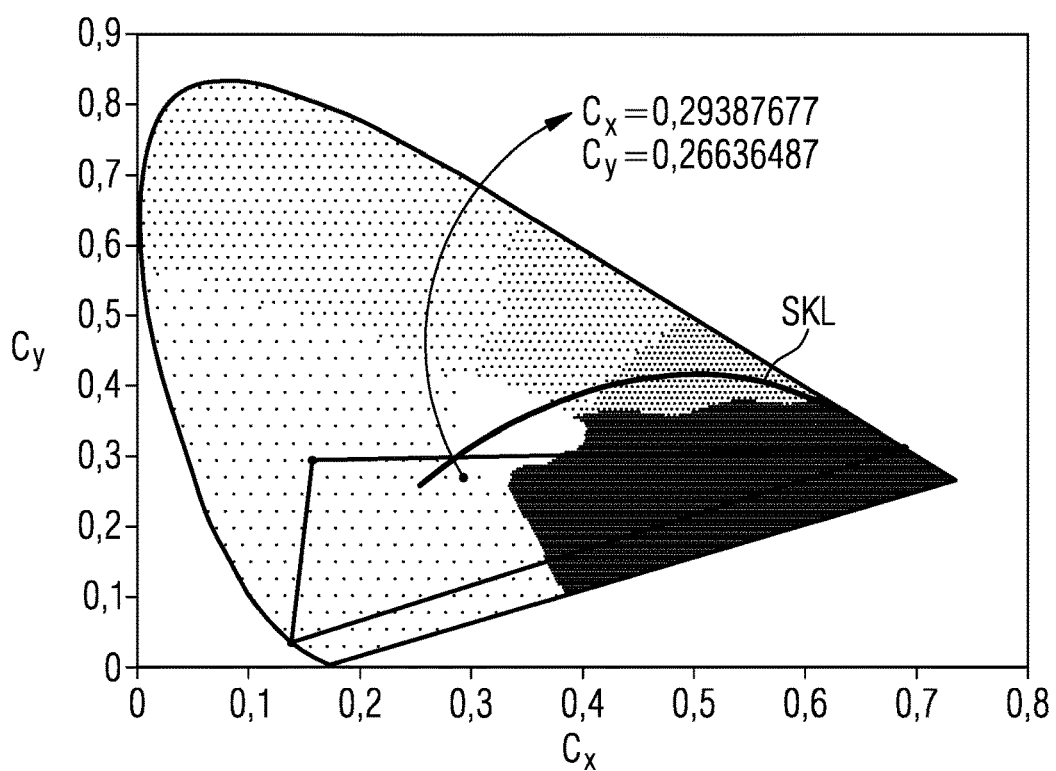

It is apparent from FIG. 9C that the color point of the white total radiation G is within a color region which is around the line of the blackbody radiator (SKL) with a deviation of up to ±0.02 $C_x$ and ±0.02 $C_y$.

The table in FIG. 9B gives proportions of photons emitted in the total radiation from the component at relative absorbances of green algae. For example, 68% of the photons emitted in the total radiation G from the component are within a wavelength range in which the relative absorption of the leaf dye of a green alga is 0.5, i.e. 10%, based on the maximum absorption. The irradiation of green algae with the total radiation from the optoelectronic component in this embodiment can efficiently stimulate these to photosynthesize and hence to grow.

Figure 10:
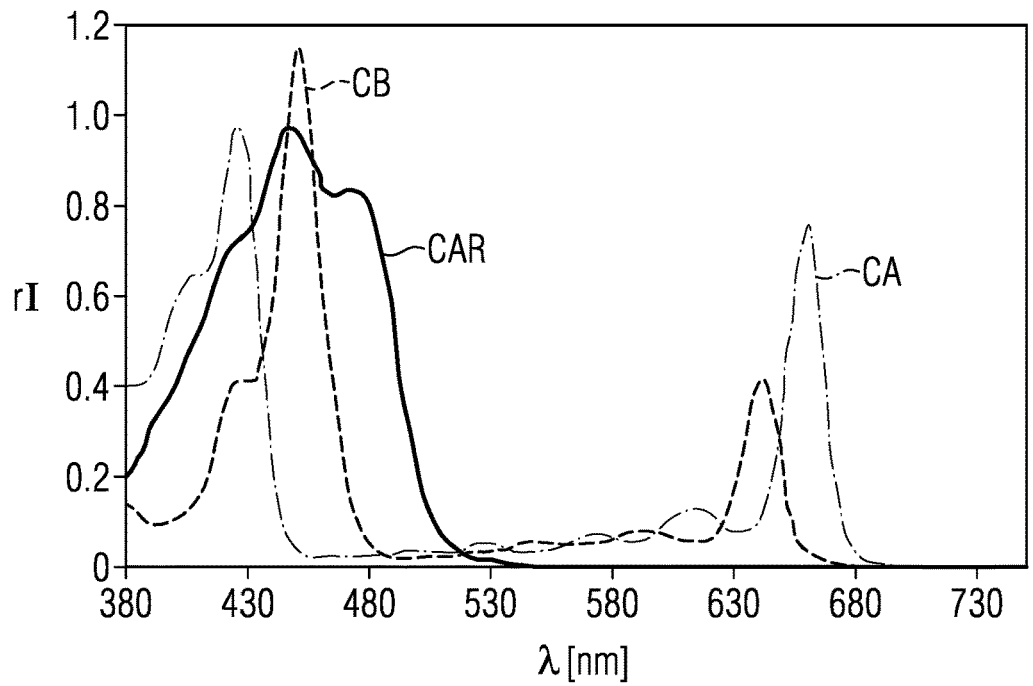
FIG. 10 shows the absorption spectrum of chlorophyll A, chlorophyll B and a carotenoid.

FIG. 10 shows absorption spectra of chlorophyll A (reference sign CA), of chlorophyll B (reference sign CB) and of a carotenoid (reference sign CAR) from Ustin et al., Remote Sensing of Environment 113, Supplemental 1, 2009, S67-S77.

Figure 11:
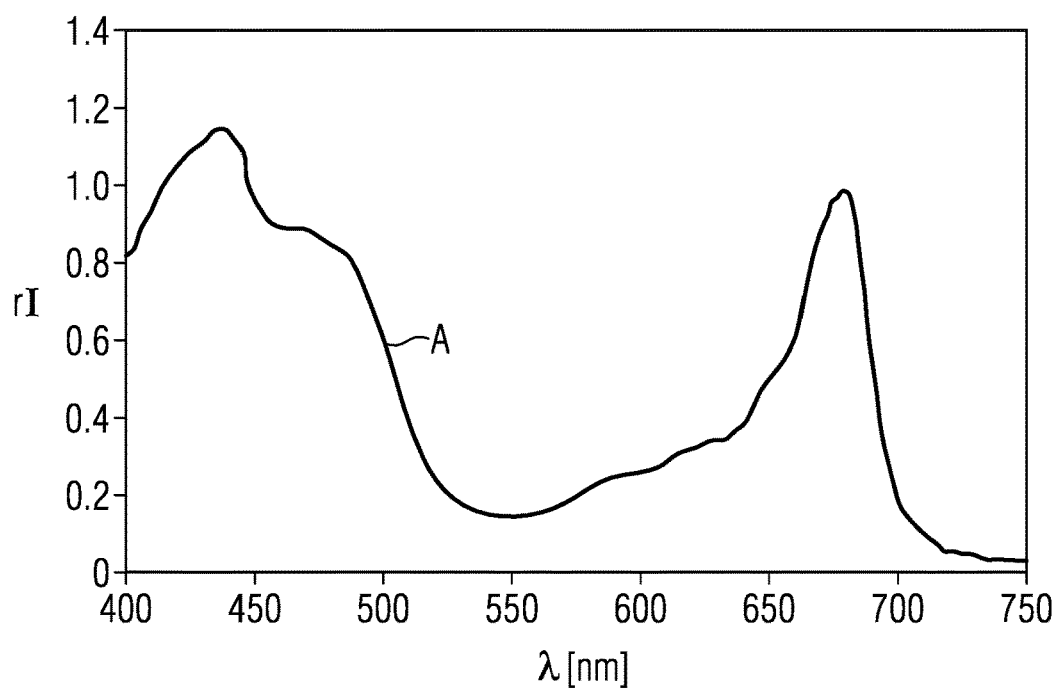
FIG. 11 shows the absorption spectrum of *Scenedesmus acutos*.

FIG. 11 shows the absorption spectrum A of a green alga using the example of Scenedesmus acutus from Zeinalov et al., Bulg. J. Plant Physiol., 2000, 26(1-2), 58-59.

Figure 12:
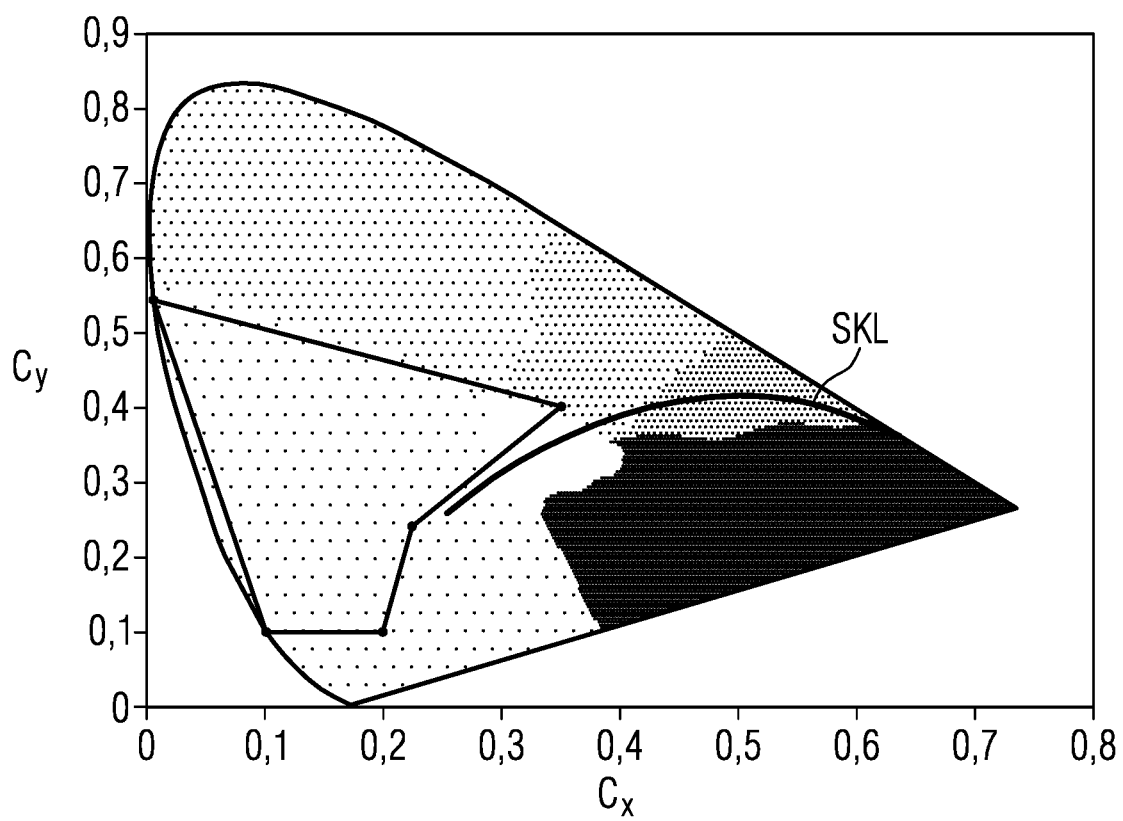
FIG. 12 shows a color region in the green region in the CIE color diagram (1931).

FIG. 12 shows a color region in the CIE color diagram (1931) which is defined by the vertices $C_x/C_y$=0.1/0.1; 0.2/0.1; 0.225/0.24; 0.35/0.4 and 0.00817/0.547. In this color region, the color point of the total radiation from a radiation-emitting optoelectronic component is in the green region of the electromagnetic spectrum.

While specific aspects have been described, it should be understood by those skilled in the art that various changes in form and detail may be made therein without departing from the spirit and scope of the aspects of this disclosure as defined by the appended claims. The scope is thus indicated by the appended claims and all changes that come within the meaning and range of equivalency of the claims are therefore intended to be embraced.

LIST OF REFERENCE SIGNS $C_x$ x component of the red base color in the CIE color space (1931)
$C_y$ y component of the green base color in the CIE color space (1931)
λ wavelength
rI relative intensity
IM relative intensity maximum
G total radiation spectrum
A absorption of Scenedesmus acutus
CA absorption of chlorophyll A
CB absorption of chlorophyll B
CAR absorption of a carotenoid
rA relative absorption
P photons emitted
$P_b$ peak wavelength of the semiconductor chip
$P_g$ peak wavelength of the first phosphor
$P_r$ peak wavelength of the second phosphor
1 radiation-emitting optoelectronic component
2 semiconductor chip
2a radiation exit surface
3 conversion element
4 first contact
4a via
5 second contact
5a via
10 base housing
11 recess
SKL blackbody radiator line

The invention claimed is:

1. A radiation-emitting optoelectronic component comprising:
a semiconductor chip or a semiconductor laser which, in operation of the component, emits a primary radiation in the UV region or in the blue region of the electromagnetic spectrum, and a conversion element comprising:
a first phosphor configured to convert the primary radiation at least partly to a first secondary radiation having a peak wavelength in the electromagnetic spectrum ranging from 475 nm to 500 nm inclusive; and wherein the first phosphor is selected from a group comprising BaSi$_4$Al$_3$N$_9$, SrSiAl$_2$O$_3$N$_2$, ALi$_3$XO$_4$ or where the first phosphor comprises a combination of at least two of the following phosphors: BaSi$_4$Al$_3$N$_9$, SrSiAl$_2$O$_3$N$_2$, BaSi$_2$N$_2$O$_2$, ALi$_3$XO$_4$ and M*$_{(1-x^*-y^*-z^*)}$Z*$_{z^*}$[A*$_{a^*}$B*$_{b^*}$C*$_{c^*}$D*$_{d^*}$E*$_{e^*}$N$_{4-n^*}$O$_{n^*}$],
wherein A is at least one element selected from the group consisting of Li, Na, K, Rb, Cs, and combinations thereof;
wherein X is at least one element selected from the group consisting of Si, Ge, Ti, Zr, Hf and combinations thereof;
wherein M* is selected from the group including Ca, Sr, Ba and combinations thereof;
wherein Z* is selected from the group including Na, K, Rb, Cs, Ag and combinations thereof;
wherein A* is selected from the group including Mg, Mn, Zn and combinations thereof;
wherein B* is selected from the group including B, Al, Ga and combinations thereof;
wherein C* is selected from the group including Si, Ge, Ti, Zr, Hf and combinations thereof;
wherein D* is selected from the group including Li, Cu and combinations thereof;
wherein E* is selected from the group including P, V, Nb, Ta and combinations thereof;
and wherein:

$0 \leq x^* \leq 0.2$;

$0 \leq y^* \leq 0.2$;

$0 \leq x^* + y^* \leq 0.4$;

$0 \leq z^* < 1;$ $0 \leq n^* \leq 4;$ $0 \leq a^* \leq 4;$ $0 \leq b^* \leq 4;$ $0 \leq c^* \leq 4;$ $0 \leq d^* \leq 4;$ $0 \leq e^* \leq 4;$ $a^*+b^*+c^*+d^*+e^*=4;$ $2a^*+3b^*+4c^*+d^*+5e^*=10-y^*-n^*+z^*;$ wherein $BaSi_4Al_3N_9$, $SrSiAL_2O_3N_2$, $BaSi_2N_2O_2$, $ALi_3XO_4$ and $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ may each independently be doped with a rare earth element; and a second phosphor configured to convert the primary radiation at least partly to a second secondary radiation having a peak wavelength in the red region of the electromagnetic spectrum from 600 nm to 700 nm inclusive and wherein the second phosphor is selected from a group comprising:
$(MgO)_{4-s}(MgF_2)_sGeO_2:Mn^{4+}$ where $0 \leq s \leq 4$,
$A'_2Ge_4O_9:Mn^{4+}$ or $A'_3A''Ge_8O_{18}:Mn^{4+}$, where A and $A'$=Li, Na, K and/or Rb $M'_{1-y'-z}Z_zG_g(BE)_b(CE)_c(DE)_dE_eN_{4-n}O_n:(RE)_{y'}$ where $M'$=Ca, Sr and/or Ba; Z=Na, K and/or Rb; G=Mg, Mn and/or Zn; BE=B, Al and/or Ga; CE=Si, Ge, Ti and/or Hf; DE=Li and/or Cu; E=P, V, Nb and/or Ta; RE=Eu and/or Yb; with $0 \leq y' \leq 0.2$; $0 \leq z < 1$; $0 \leq n \leq 0.5$; $0 \leq g \leq 4$; $0 \leq b \leq 4$; $0 \leq c \leq 4$; $0 \leq d \leq 4$; $0 \leq e \leq 4$; g+b+c+d+e=4; and 2g+3b+4c+d+5e=10-y'-n+z, and combinations thereof.

2. The radiation-emitting optoelectronic component as claimed in claim 1,
wherein the primary radiation is converted fully to the first secondary radiation and the component emits total radiation having a peak wavelength in the electromagnetic spectrum ranging from 475 nm to 500 nm inclusive.

3. The radiation-emitting optoelectronic component as claimed in claim 2,
wherein the color point of the total radiation is within a color region defined in the CIE color diagram (1931) by the vertices Cx/Cy=0.1/0.1; 0.2/0.1; 0.225/0.24; 0.35/0.4 and 0.00817/0.547.

4. The radiation-emitting optoelectronic component as claimed in claim 1,
wherein the conversion element comprises a second phosphor configured to convert the primary radiation at least partly to a second secondary radiation having a peak wavelength in the red region of the electromagnetic spectrum from 600 nm to 700 nm inclusive; and wherein the second phosphor is selected from a group comprising $(Ca,Sr)AlSiN_3:Eu^{2+}$, $(Ca,Sr)AlSiN_3:Yb^{2+}$; $(Sr,Ca)_3Al_2O_3:Eu^{2+}$; $(Sr, Ca,Ba)_2Si_5N_8:Eu^{2+}$; $SrSiN_2:Eu^{2+}$; $SrAlSi_4N_7:Eu^{2+}$; $CaSi_2Al_2N_8:Eu^{2+}$; $CaS:Eu^{2+}$; $Sr[LiAl_3N_4]:Eu^{2+}$; $Sr[LiAl_3N_4]:Yb^{2+}$; $K_2Ge_4O_9:Mn^{4+}$; $Rb_2Ge_4O_9:Mn^{4+}$; $Li_3RbGe_8O_{18}:Mn^{4+}$; $Sr_4Al_{14}O_{25}:Mn^{4+}$; $Mg_2TiO_4:Mn^{4+}$; $CaZrO_3:Mn^{4+}$; $Gd_3Ga_5O_{12}:Mn^{4+}$; $Al_2O_3:Mn^{4+}$; $GdAlO_3:Mn^{4+}$; $LaAlO_3:Mn^{4+}$; $LiAl_5O_8:Mn^{4+}$; $SrTiO_3:Mn^{4+}$; $Y_2Ti_2O_7:Mn^{4+}$; $Y_2Sn_2O_7:M^{n+}$; $CaAl_{12}O_{19}:Mn^{4+}$; $MgO:Mn^{4+}$; $Ba_2LaNbO_6:Mn^{4+}$; $K_2SiF_6:Mn^{4+}$; $Na_2SiF_6:Mn^{4+}$; $K_2TiF_6:Mn^{4+}$; $Mg_4GeO_{5.5}F:Mn^{4+}$, and combinations thereof.

5. The radiation-emitting optoelectronic component as claimed in claim 1, wherein the first phosphor has the formula $BaSi_4Al_3N_9:Eu^{2+}$ and the second phosphor has the formula $Mg_4GeO_{5.5}F:Mn^{4+}$, the first phosphor has the formula $BaSi_4Al_3N_9:Eu^{2+}$ and the second phosphor has the formula $K_2SiF_6:Mn^{4+}$, the first phosphor has the formula $ALi_3XO_4:Eu^{2+}$ and the second phosphor has the formula $K_2SiF_6:Mn^{4+}$, or the first phosphor has the formula $SrSiAl_2O_3N_2:Eu^{2+}$ and the second phosphor has the formula $K_2SiF_6:Mn^{4+}$.

6. The radiation-emitting optoelectronic component as claimed in claim 1,
wherein the primary radiation is converted partly to the first and second secondary radiations and the component emits a white total radiation and the spectrum of the total radiation has at least three and at most five intensity maxima in the range from 400 nm to 800 nm inclusive.

7. The radiation-emitting optoelectronic component as claimed in claim 6,
wherein at least one intensity maximum in each case is in the range from 400 nm to 475 nm inclusive, in the range from 475 nm to 500 nm inclusive and in the range from 600 nm to 700 nm inclusive.

8. The radiation-emitting optoelectronic component as claimed in claim 6,
wherein there is no intensity maximum in the range from 500 nm to 600 nm.

9. The radiation-emitting optoelectronic component as claimed in claim 6,
wherein the color point of the white total radiation is in a color region which, in the CIE color diagram (1931), lies on the line of the blackbody radiator or with a deviation of up to $\pm 0.02$ $C_X$ and/or $\pm 0.02$ $C_y$ from the line of the blackbody radiator.

10. The radiation-emitting optoelectronic component as claimed in claim 6,
wherein the color temperature of the white total radiation is from 30 000 K to 2700 K inclusive.

11. A radiation-emitting optoelectronic component comprising:
a semiconductor chip or a semiconductor laser which, in operation of the component, emits a primary radiation in the UV region or in the blue region of the electromagnetic spectrum; and
a further semiconductor chip or a further semiconductor laser which, in operation of the component, emits a primary radiation having a peak wavelength in the electromagnetic spectrum from 475 nm to 500 nm inclusive, and
a conversion element comprising a second phosphor configured to convert the primary radiation at least partly to a second secondary radiation having a peak wavelength in the red region of the electromagnetic spectrum from 600 nm to 700 nm inclusive, and wherein the second phosphor is selected from a group comprising:
$A'_2Ge_4O_9:Mn^{4+}$ or $A'_3A''Ge_8O_{18}:Mn^{4+}$, where A and $A'$=Li, Na, K and/or Rb;
$M'_{1-y'-z}Z_zG_g(BE)_b(CE)_c(DE)_dE_eN_{4-n}O_n:(RE)_{y'}$, where $M'$=Ca, Sr and/or Ba; Z=Na, K and/or Rb; G=Mg, Mn and/or Zn; BE=B, Al and/or Ga; CE=Si, Ge, Ti and/or Hf; DE=Li and/or Cu; E=P, V, Nb and/or Ta; RE=Eu and/or Yb; with $0 \leq y' \leq 0.2$; $0 \leq z < 1$; $0 \leq n \leq 0.5$; $0 \leq g \leq 4$; $0 \leq b \leq 4$; $0 \leq c \leq 4$; $0 \leq d \leq 4$; $0 \leq e \leq 4$; $g+b+c+d+e=4$; and $2g+3b+4c+d+5e=10-y'-n+z$; and combinations thereof.

12. The component as claimed in claim 1, wherein the first phosphor is selected from a group comprising $BaSi_4Al_3N_9$, $SrSiAl_2O_3N_2$, $ALi_3XO_4$, and combinations thereof;

wherein A is at least one element selected from the group consisting of Li, Na, K, Rb, Cs, and combinations thereof; and wherein X is at least one element selected from the group consisting of Si, Ge, Ti, Zr, Hf, and combinations thereof.

13. The component as claimed in claim 1, wherein $ALi_3XO_4$ is selected from a group comprising $NaLi_3SiO_4:Eu^{2+}$, $NaK(Li_3SiO_4)_2:Eu^{2+}$, $RbNa_3(Li_3SiO_4)_4:Eu^{2+}$, $CsKNa_2(Li_3SiO_4)_4:Eu^{2+}$, $RbKNa_2(Li_3SiO_4)_4:Eu^{2+}$, and $CsRbNaLi(Li_3SiO_4)_4:Eu^{2+}$.

14. A radiation-emitting optoelectronic component comprising:

a semiconductor chip or a semiconductor laser which, in operation of the component, emits a primary radiation in the UV region or in the blue region of the electromagnetic spectrum; and a further semiconductor chip or a further semiconductor laser which, in operation of the component, emits a primary radiation in the red region of the electromagnetic spectrum from 600 nm to 700 nm inclusive, and a conversion element comprising a first phosphor configured to convert the primary radiation at least partly to a first secondary radiation having a peak wavelength in the electromagnetic spectrum from 475 nm to 500 nm inclusive, and wherein the first phosphor comprises at least $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$, and combinations thereof;

wherein A is at least one element selected from the group consisting of Li, Na, K, Rb, Cs and combinations thereof;

wherein X is at least one element selected from the group consisting of Si, Ge, Ti, Zr, Hf and combinations thereof;

wherein M* is selected from the group comprising of Ca, Sr, Ba and combinations thereof;

wherein Z* is selected from the group comprising of Na, K, Rb, Cs, Ag and combinations thereof;

wherein A* is selected from the group comprising of Mg, Mn, Zn and combinations thereof;

wherein B* is selected from the group comprising of B, Al, Ga and combinations thereof;

wherein C* is selected from the group comprising of Si, Ge, Ti, Zr, Hf and combinations thereof;

wherein D* is selected from the group comprising of Li, Cu and combinations thereof;

wherein E* is selected from the group comprising of P, V, Nb, Ta and combinations thereof; and wherein:

$0 \leq x^* \leq 0.2$;

$0 \leq y^* \leq 0.2$;

$0 \leq x^* + y^* \leq 0.4$;

$0 \leq z^* < 1$;

$0 \leq n^* \leq 4$;

$0 \leq a^* \leq 4$;

$0 \leq b^* \leq 4$;

$0 \leq c^* \leq 4$;

$0 \leq d^* \leq 4$;

$0 \leq e^* \leq 4$;

$a^*+b^*+c^*+d^*+e^*=4$;

$2a^*+3b^*+4c^*+d^*+5e^*=10-y^*-n^*+z^*$;

wherein the first phosphor is a combination including at least one additional phosphor selected from the group consisting of $BaSi_4Al_3N_9$, $SrSiAl_2O_3N_2$, $BaSi_2N_2O_2$, and $ALi_3XO_4$, wherein $BaSi_4Al_3N_9$, $SrSiAl_2O_3N_2$, $BaSi_2N_2O_2$, $ALi_3XO_4$ and $M^*_{(1-x^*-y^*-z^*)}Z^*_{z^*}[A^*_{a^*}B^*_{b^*}C^*_{c^*}D^*_{d^*}E^*_{e^*}N_{4-n^*}O_{n^*}]$ may each independently be doped with a rare earth element.

* * * * *